(12) United States Patent
Parsons et al.

(10) Patent No.: US 7,238,703 B2
(45) Date of Patent: Jul. 3, 2007

(54) AZABICYCLIC, AZATRICYCLIC AND AZASPIROCYCLIC DERIVATIVES OF AMINOCYCLOHEXANE NMDA, 5HT$_3$, AND NEURONAL NICOTINIC RECEPTOR ANTAGONISTS

(75) Inventors: Christopher G. R. Parsons, Nidderau (DE); Markus Henrich, Wetzlar (DE); Wojciech Danysz, Nidderau (DE); Ivars Kalvinsh, Salaspils (LV); Valerjans Kauss, Riga (LV); Aigars Jirgensons, Riga (LV); Markus Gold, Nauheim (DE); Maksims Vanejevs, Riga (LV)

(73) Assignee: Merz Pharma GmbH & Co. KGAA, Frankfurt Main (DE)

( * ) Notice: Subject to any disclaimer, the term of this patent is extended or adjusted under 35 U.S.C. 154(b) by 0 days.

(21) Appl. No.: 11/202,012

(22) Filed: Aug. 11, 2005

(65) Prior Publication Data

US 2006/0019982 A1    Jan. 26, 2006

Related U.S. Application Data

(62) Division of application No. 10/394,670, filed on Mar. 21, 2003, now Pat. No. 7,022,729.

(60) Provisional application No. 60/366,386, filed on Mar. 21, 2002.

(51) Int. Cl.
*A61K 31/438* (2006.01)
*C07D 221/20* (2006.01)

(52) U.S. Cl. ................. 514/278; 546/16; 548/408; 540/543; 514/409

(58) Field of Classification Search ............... 514/278, 514/409; 546/16; 548/408; 540/543
See application file for complete search history.

(56) References Cited

U.S. PATENT DOCUMENTS 5,936,088 A    8/1999   Olesen

FOREIGN PATENT DOCUMENTS

| EP | 0018077 | 10/1980 |
|---|---|---|
| EP | 0072438 | 2/1983 |
| EP | 0578560 | 1/1994 |
| GB | 1153973 | 6/1969 |
| GB | 1472334 | 5/1977 |
| WO | WO 92/12149 | 7/1992 |
| WO | WO 94/08964 | 4/1994 |
| WO | WO 96/06081 | 2/1996 |
| WO | WO 00/32600 | 6/2000 |
| WO | WO 01/98253 | 12/2001 |

OTHER PUBLICATIONS

R.L. Frank, H.K. Hall (1950) J. Am. Chem. Soc. 72:1645-1648.
G.A. Hiegel, P. Burk. (1973) J. Org. Chem. 38:3637-3639.
N.F. Firrell, P.W. Hickmott. (1970) J. Chem. Soc. C:716-719.
G.H. Posner, L.L. Frye. (1984) Isr. J. Chem. 24:88-92.
G.L. Lemiere, T.A. van Osselaer, F.C. Anderweireldt. (1978) Bull. Soc. Chim. Belg. 87:771-782.
H.O. House, J.M. Wilkins. (1976) J. Org. Chem. 41:(25) 4031-4033.
A.R. Greenaway, W.B. Whalley. (1976) J. Chem. Soc. P.T. 1.:1385-1389.
S. Matsuzawa, Y. Horiguchi, E. Nakamura, I. Kuwajima. (1989) Tetrahedron 45:(2) 349-362.
H.O. House, W.F. Fischer. (1968) J. Org. Chem. 33:(3) 949-956.
Chiurdoglu, G., Maquestiau, A. (1954) Bull. Soc. Chim. Belg. 63: 357-378.
Zaidlewicz, M., Uzarewicz A., Zacharewicz, W. (1964) Roczniki Chem. 38: 591-597.
Crossley, A.W., Gilling, C. (1910) J. Chem. Soc. 2218.
Zaidlewicz, M., Uzarewicz, A. (1971) Roczniki Chem. 45: 1187-1194.
Lutz, E.T., van der Maas, J.H. (1981) Spectrochim. Acta, A. 38A:283.
Lutz, E.T., van der Maas, J.H. (1981) Spectrochim. Acta, A. 37A: 129-134.
Ramalingam K., Balasubramanian, M., Baliah, V. (1972) Indian J. Chem. 10: 366-369.
Hamlin, K.E., Freifelder, M. (1953) J. Am. Chem. Soc. 75: 369-373.
Hassner, A., Fibinger, R., Andisik, D. (1984) J. Org. Chem. 49: 4237-4244.
W. Danysz, C.G. Parsons, I. Bresink, G. Quack (1995) Drug News Perspect. 8:261-277.
J.D. Leander, R.R. Lawson, P.L., Ornstein, D.M. Zimmerman (1988) Brain Res. 448:115-120.
C.G. Parsons, G. Quack, I. Bresink, L. Baran, E. Przegalinski, W. Kostowski, P. Krzascik, S. Hartmann, W. Danysz (1995). Neuropharmacology 34:1239-1258.
M.A. Rogawski (1993) Trends Pharmacol. Sci. 14:325-331.
Booher J. and Sensenbrenner M. (1972). Neurobiology 2:97-105.
Dichter, M. (1987) Brain Research 149:279.
Parsons, et al., *Drug News Perspect.*, Nov. 1998, 11, 523-569.
Brunson, et al., *Dev. Neurosci.*, 2001, 23, 31-40 (abstract).
Hadj, et al., *Neurobiol. Dis.*, 2004, 15, 171-176 (abstract).
Javitt, *Mol. Psychiatry*, 2004, [Epub ahead of print] (abstract).
Paquet-Durand, et al., 2004, 1011, 33-47 (abstract).
Hare, et al., *Invest. Ophthalmol. Vis. Sci.*, 2004, 45, 2625-2639 (abstract).
Rosin, et al., *J. Neurochem.*, 2004, 90, 1173-1185 (abstract).
Dirson, et al., *Metab. Brain Dis.*, 2002, 17, 77-82 (abstract).
Petri, et al., *Neurosci. Lett.*, 2004, 360, 170-174 (abstract).

(Continued)

*Primary Examiner*—Charanjit S. Aulakh
(74) *Attorney, Agent, or Firm*—Hueschen and Sage

(57) ABSTRACT

Azabicyclic, azatricyclic and azaspirocyclic derivatives of aminocyclohexanes which are systemically-active as NMDA, 5HT$_3$, and nicotinic receptor antagonists, pharmaceutical compositions comprising the same, method of preparation thereof, and method of treating CNS disorders which involve disturbances of glutamatergic, serotoninergic, and nicotinic transmission, treating immunomodulatory disorders, and antimalaria, antitrypanosomal, anti-Borne virus, anti-HSV and anti-Hepatitis C virus activity.

3 Claims, 2 Drawing Sheets

OTHER PUBLICATIONS

Khodorov, *Prog. Biophys. Mol. Biol.*, 2004, 86, 279-351 (abstract).
Tsai, et al., *Am. J. Psychiatry*, 1995, 152, 332-340 (abstract).
Ferrer, et al., *Acta Neuropathol.*, 2003, 106, 311-318 (abstract).
Greenshaw, *TiPS*, 1993, 14, 265-270.
Dahlof, et al., *Cephalalgia*, 1998, 18, 593-604 (abstract).
Talley, *Br. J. Clin. Pharmacol.*, 2003, 56, 362-369 (abstract).
Deakin, *Int. Clin. Psychopharmacol.*, 1991, *6 Suppl 3*, 23-31 (abstract).
Meltzer, *Schizophr. Bull.*, 1991, 17, 263-287 (abstract).
Gbadamosi, et al., *Acta. Neurol. Scand.*, 2001, 104, 308-311 (abstract).
Quick, et al., *Desensitization of Neuronal Nicotinic Receptors*, 2002, Wiley Periodicals, Inc., 457-478.
LLoyd, et al., *Life Sciences*, 1998, 62, 1601-1606.
Mc Evoy, et al., *Curr. Drug Targets CNS Neurol. Disord.*, 2002, 1, 433-442 (abstract).
Newhouse, et al., *Curr. Top Med. Chem.*, 2004, 4, 267-282 (abstract).
*Patent Abstracts of Japan*, vol. 012, No. 192 (P-712), Jun. 4, 1988.
*Beilstein Crossfire Database abstract* Accession Nos. 5577766(brn); 5586551(brn); 5615067(brn).
Darwish, et al., *Chemical Abstracts*, Accession No. 97:2169.
*Chemical Abstracts Chemcats Database*, Accession No. 2002:3093676.
*Chemical Abstracts, Database Accession* No. 121: 205227.
Deakin, *Int. Clin. Psychopharmacol.*, 1991, *6 Suppl 3*, 23-31 (abstract).

| Parameter | Value | Std. Error |
|---|---|---|
| IC 50 | 6.1308 | 0.4393 |
| Slope factor | 1.1338 | 0.0783 |

MRZ 2/1013

| Parameter | Value | Std. Error |
|---|---|---|
| IC 50 | 7.0540 | 0.6228 |
| Slope factor | 0.9762 | 0.0731 |

MRZ 2/1003

| Parameter | Value | Std. Error |
|---|---|---|
| IC 50 | 13.9625 | 1.6508 |
| Slope factor | 1.0367 | 0.1136 |

MRZ 2/1004

| Parameter | Value | Std. Error |
|---|---|---|
| IC 50 | 27.5514 | 3.0482 |
| Slope factor | 0.9117 | 0.0835 |

AZABICYCLIC, AZATRICYCLIC AND AZASPIROCYCLIC DERIVATIVES OF AMINOCYCLOHEXANE NMDA, 5HT$_3$, AND NEURONAL NICOTINIC RECEPTOR ANTAGONISTS

BACKGROUND OF THE INVENTION

1. Field of the Invention

Azabicyclic, azatricyclic and azaspirocyclic derivatives of aminocyclohexanes which are systemically-active as NMDA, 5HT$_3$, and nicotinic receptor antagonists, pharmaceutical compositions comprising the same, method of preparation thereof, and method of treating CNS disorders which involve disturbances of glutamatergic, serotoninergic, and nicotinic transmission therewith, for treating immunomodulatory disorders, and for treating infectious diseases.

2. Prior Art

NMDA Antagonists

Antagonism of glutamate receptors of the N-methyl-D-aspartate (NMDA) type has a potentially wide range of therapeutic applications [19]. Functional inhibition of NMDA receptors can be achieved through actions at different recognition sites such as the primary transmitter site, strychnine-insensitive glycine site (glycine$_B$), polyamine site, and phencyclidine site located inside the cation channel. The NMDA receptor channel blockers act in an uncompetitive "use-dependent" manner, meaning that they usually only block the channel in the open state. This use-dependence has been interpreted by many to mean that stronger activation of the receptor should lead to a greater degree of antagonism. Such a mode of action has further been taken to imply that this class of antagonist may be particularly useful when overactivation of NMDA receptors can be expected, such as in epilepsy, ischemia, and trauma. However, initial clinical experience with the selective, high affinity, strongly use-dependent uncompetitive NMDA receptor antagonist (+)-5-methyl-10,11-dihydro-5H-dibenzocyclohepten-5,10-imine maleate ((+)-MK-801) has been disappointing. Namely, therapeutic efficacy in epilepsy was poor while some psychotropic side effects were apparent at therapeutic doses. These observations, together with the fact that phencyclidine abusers experience similar psychotropic symptoms, has led to the conclusion that uncompetitive antagonism of NMDA receptors may not be a promising therapeutic approach.

However, the use of more elaborate electrophysiological methods indicates that there is no equality between different uncompetitive antagonists since factors such as the speed of receptor blockade (on-off kinetics) and the voltage-dependence of this effect may determine the pharmacodynamic features in vivo, i.e., therapeutic safety as well. Paradoxically, agents with low to moderate, rather than high, affinity may be desirable. Such findings triggered a reconsideration of the concept of uncompetitive antagonism of NMDA receptors in drug development [19, 22]. Uncompetitive NMDA receptor antagonists, such as amantadine and mezzanine—which fulfill the above criteria—have been used clinically for several years in the treatment of Parkinson's disease and dementia respectively, and do indeed rarely produce side effects at the therapeutic doses used in their respective indications.

In view of the above mentioned evidence, we have developed a series of novel uncompetitive NMDA receptor antagonists based on the azabicyclic, azatricyclic and azaspirocyclic aminocyclohexane structure.

5-HT$_3$ Receptor Antagonists

5-HT$_3$ receptors are ligand gated ionotropic receptors permeable for cations. In man 5-HT$_3$ receptors show the highest density on enterochromaffin cells in the gastrointestinal mucosa, which are innervated by vagal afferents and the area postrema of the brain stem, which forms the chemoreceptor trigger zone.

Since 5-HT$_3$ receptors not only have a high density in the area postrema but also in the hippocampal and amygdala region of the limbic system, it has been suggested that 5-HT$_3$ selective antagonists may have psychotropic effects (Greenshaw & Silverstone, 1997).

Indeed, early animal studies suggested that the 5-HT$_3$ receptor antagonists, in addition to their well recognized anti-emetic use, may well be clinically useful in a number of areas. These include anxiety disorders, schizophrenia, drug and alcohol abuse disorders, depressive disorders, cognitive disorders, Alzheimer's disease, cerebellar tremor, Parkinson's disease treatment-related psychosis, pain (migraine and irritable bowel syndrome), and appetite disorders.

Neuronal Nicotinic Receptor Antagonists

At present, ten alpha subunits (alpha 1-10) and four beta subunits (beta 1-4) for nicotinic receptors are known. α4β2 receptors are probably the most common in the CNS, especially in the hippocampus and striatum. They form non-selective cation channels with slowly, incompletely desensitizing currents (type II). Homomeric α7 receptors are both pre- and postsynaptic and are found in the hippocampus, motor cortex and limbic system as well as in the peripheral autonomic nervous system. These receptors are characterized by their high Ca$^{2+}$ permeability and fast, strongly desensitizing responses (type 1A). Changes in nicotinic receptors have been implicated in a number of diseases. These include Alzheimer's disease, Parkinson's disease, Tourette's syndrome, schizophrenia, drug abuse, nicotine abuse, and pain.

Based on the observation that the nicotinic agonist nicotine itself seems to have beneficial effects, drug development so far is aimed at the discovery of selective nicotinic agonists.

On the other hand, it is unclear whether the effects of nicotinic agonists in, e.g., Tourette's syndrome and schizophrenia, are due to activation or inactivation/desensitization of neuronal nicotinic receptors.

The effects of agonists on neuronal nicotinic receptors is strongly dependent on the exposure period. Rapid reversible desensitization occurs in milliseconds, rundown occurs in seconds, irreversible inactivation of α4β2 and α7 containing receptors occurs in hours and their upregulation occurs within days.

In other words, the effects of nicotinic "agonists" may in fact be due to partial agonism, inactivation and/or desensitization of neuronal nicotinic receptors. In turn, moderate concentrations of neuronal nicotinic receptor channel blockers could produce the same effects as reported for nicotinic agonists in the above mentioned indications.

THE PRESENT INVENTION

It has now been found that certain azabicyclic, azatricyclic and azaspirocyclic derivatives of aminocyclohexanes have pronounced and unpredictable NMDA, 5HT$_3$, and nicotinic receptor antagonistic activity. Owing to the aforementioned property, the substances are suited for the treatment of a wide range of CNS disorders which involve disturbances of glutamatergic, serotoninergic, and nicotinic transmission, immunomodulatory effect, and anti-infectious diseases properties. These compounds are preferably in the form of a pharmaceutical composition thereof wherein they are present together with one or more pharmaceutically-acceptable diluents, carriers, or excipients.

OBJECTS OF THE INVENTION

It is an object of the present invention to provide novel pharmaceutical compounds which are azabicyclic, azatricyclic and azaspirocyclic aminocyclohexane NMDA, 5HT$_3$, and nicotinic receptor antagonists and pharmaceutical compositions thereof. It is a further object of the invention to provide a novel method of treating, eliminating, alleviating, palliating, or ameliorating undesirable CNS disorders which involve disturbances of glutamatergic, serotoninergic, nicotinic transmission, for treating immunomodulatory disorders, and for treating infectious diseases by employing a compound of the invention or a pharmaceutical composition containing the same. An additional object of the invention is the provision of a process for producing the azabicyclic, azatricyclic and azaspirocyclic aminocyclohexane active principles. Yet additional objects will become apparent hereinafter, and still further objects will be apparent to one skilled in the art.

SUMMARY OF THE INVENTION

What we therefore believe to be comprised by our invention may be summarized inter alia in the following words:

A compound selected from those of formula 1,

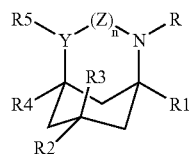

1 wherein

R is selected from the group consisting of hydrogen, straight or branched chain alkyl (C$_1$-C$_6$), straight or branched chain alkenyl (C$_2$-C$_6$), straight or branched chain alkynyl (C$_2$-C$_6$), aryl, substituted aryl, and arylalkyl;

R$^1$ is selected from the group consisting of straight or branched chain alkyl (C$_1$-C$_6$), straight or branched chain alkenyl (C$_2$-C$_6$), straight or branched chain alkynyl (C$_2$-C$_6$), aryl, substituted aryl, and arylalkyl;

R$^2$ through R$^5$ are independently selected from the group consisting of hydrogen, straight or branched chain alkyl (C$_1$-C$_6$), straight or branched chain alkenyl (C$_2$-C$_6$), straight or branched chain alkynyl (C$_2$-C$_6$), aryl, substituted aryl, and arylalkyl;

Z is CH$_2$;

N=0 or 1;

Y=CH;

and provided that at least one of R$^2$ and R$^3$ are not hydrogen and at least one of R$^4$ and R$^5$ are not hydrogen;

or those compounds wherein R and R$^1$ combine to form a C$_3$-C$_5$ alkylene or alkenylene bridge U-V-W-X, resulting in the structure represented by formula 2,

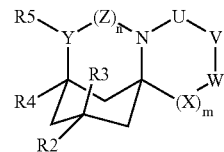

2 wherein X=CH$_2$ or CH;

m=0, 1, 2;

or those compounds wherein R and R$^1$ combine to form a C$_3$-C$_5$ alkylene or alkenylene bridge U—V—W—X, and ring members N and Y do not connect to form a bridge, resulting in the basic structure represented by formula 3

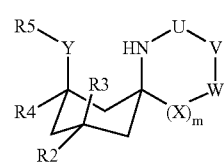

3 wherein ring member N is saturated and ring member Y is saturated or may combine together with R5 to form a carbon-hydrogen bond with the ring carbon to which it is attached;

its optical isomers and pharmaceutically-acceptable acid or base addition salt thereof;

such a method-of-treating a living animal for alleviation of a condition wherein the compound is selected for its immunomodulatory, anti-malarial, anti-Borne virus, or anti-Hepatitis C, anti-trypanosomal, and anti-HSV efficacy, comprising the step of administering to the living animal an amount of a compound selected from those of formula 1,

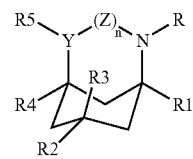

1 wherein

R is selected from the group consisting of hydrogen, straight or branched chain alkyl (C$_1$-C$_6$), straight or branched chain alkenyl (C$_2$-C$_6$), straight or branched chain alkynyl (C$_2$-C$_6$), aryl, substituted aryl, and arylalkyl;

R$^1$ is selected from the group consisting of straight or branched chain alkyl (C$_1$-C$_6$), straight or branched chain alkenyl (C$_2$-C$_6$), straight or branched chain alkynyl (C$_2$-C$_6$), aryl, substituted aryl, and arylalkyl;

R$^2$ through R$^5$ are independently selected from the group consisting of hydrogen, straight or branched chain alkyl (C$_1$-C$_6$), straight or branched chain alkenyl (C$_2$-C$_6$), straight or branched chain alkynyl (C$_2$-C$_6$), aryl, substituted aryl, and arylalkyl;

Z is CH$_2$;

N=0 or 1;

Y=CH;

or those compounds wherein R and R¹ combine to form a C₃-C₅ alkylene or alkenylene bridge U—V—W—X, resulting in the structure represented by formula 2,

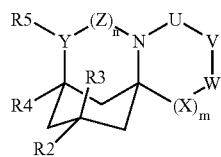

2 wherein X=CH₂;
m=0, 1, 2;

or those compounds wherein R and R¹ combine to form a C₃-C₅ alkylene or alkenylene bridge U—V—W—X, and ring members N and Y do not connect to form a bridge, resulting in the basic structure represented by formula 3,

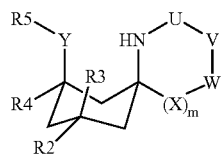

3 wherein ring member N is saturated and ring member Y is saturated or may combine together with R5 to form a carbon-hydrogen bond with the ring carbon to which it is attached;

its optical isomers and pharmaceutically-acceptable acid or base addition salt thereof;

which is effective for alleviation of said condition;

such a method-of-treating a living animal for alleviation of a condition treatable by an NMDA antagonist selected from the group consisting of excitotoxicity selected from ischemia during stroke, trauma, hypoxia, hypoglycemia, glaucoma, and hepatic encephalopathy, chronic neurodegenerative diseases selected from Alzheimer's disease, vascular dementia, Parkinson's disease, Huntington's disease, multiple sclerosis, amyotrophic lateral sclerosis, AIDS-neurodegeneration, olivopontocerebellar atrophy, Tourette's syndrome, motor neurone disease, mitochondrial dysfunction, Korsakoff syndrome, and Creutzfeldt-Jakob disease, other disorders related to long term plastic changes in the central nervous system selected from chronic pain, drug tolerance, dependence and addiction (e.g., opioids, cocaine, benzodiazepines, nicotine, and alcohol), and epilepsy, tardive dyskinesia, L-DOPA-induced dyskinesia, schizophrenia, anxiety, depression, acute pain, spasticity, and tinnitus, comprising the step of administering to the living animal an amount of a compound selected from those of formula 1,

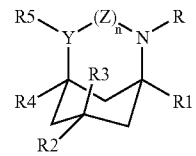

1 wherein

R is selected from the group consisting of hydrogen, straight or branched chain alkyl ($C_1$-$C_6$), straight or branched chain alkenyl ($C_2$-$C_6$), straight or branched chain alkynyl ($C_2$-$C_6$), aryl, substituted aryl, and arylalkyl;

R¹ is selected from the group consisting of straight or branched chain alkyl ($C_1$-$C_6$), straight or branched chain alkenyl ($C_2$-$C_6$), straight or branched chain alkynyl ($C_2$-$C_6$), aryl, substituted aryl, and arylalkyl;

R² through R⁵ are independently selected from the group consisting of hydrogen, straight or branched chain alkyl ($C_1$-$C_6$), straight or branched chain alkenyl ($C_2$-$C_6$), straight or branched chain alkynyl ($C_2$-$C_6$), aryl, substituted aryl, and arylalkyl;

Z is CH₂;

N=0 or 1;

Y=CH;

or those compounds wherein R and R¹ combine to form a C₃-C₅ alkylene or alkenylene bridge U—V—W—X, resulting in the structure represented by formula 2,

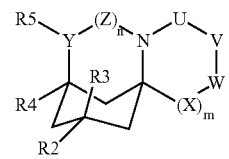

2 wherein X=CH₂;
m=0, 1, 2;

or those compounds wherein R and R¹ combine to form a C₃-C₅ alkylene or alkenylene bridge U—V—W—X, and ring members N and Y do not connect to form a bridge, resulting in the basic structure represented by formula 3,

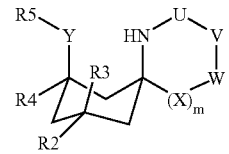

3 wherein ring member N is saturated and ring member Y is saturated or may combine together with R5 to form a carbon-hydrogen bond with the ring carbon to which it is attached;

its optical isomers and pharmaceutically-acceptable acid or base addition salt thereof;

which is effective for alleviation of said condition;

such a method-of-treating a living animal for alleviation of a condition treatable by a 5HT$_3$ receptor antagonist, comprising the step of administering to the living animal an amount of a compound selected from those of formula 1,

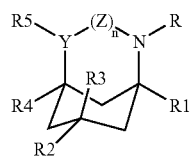

1 wherein
R is selected from the group consisting of hydrogen, straight or branched chain alkyl (C$_1$-C$_6$), straight or branched chain alkenyl (C$_2$-C$_6$), straight or branched chain alkynyl (C$_2$-C$_6$), aryl, substituted aryl, and arylalkyl;
R$^1$ is selected from the group consisting of straight or branched chain alkyl (C$_1$-C$_6$), straight or branched chain alkenyl (C$_2$-C$_6$), straight or branched chain alkynyl (C$_2$-C$_6$), aryl, substituted aryl, and arylalkyl;
R$^2$ through R$^5$ are independently selected from the group consisting of hydrogen, straight or branched chain alkyl (C$_1$-C$_6$), straight or branched chain alkenyl (C$_2$-C$_6$), straight or branched chain alkynyl (C$_2$-C$_6$), aryl, substituted aryl, and arylalkyl;
Z is CH$_2$;
N=0 or 1;
Y=CH;

or those compounds wherein R and R$^1$ combine to form a C$_3$-C$_5$ alkylene or alkenylene bridge U—V—W—X, resulting in the structure represented by formula 2,

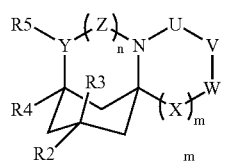

2 wherein X=CH$_2$;
m=0, 1, 2;

or those compounds wherein R and R$^1$ combine to form a C$_3$-C$_5$ alkylene or alkenylene bridge U—V—W—X, and ring members N and Y do not connect to form a bridge, resulting in the basic structure represented by formula 3,

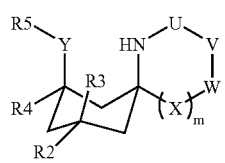

3 wherein ring member N is saturated and ring member Y is saturated or may combine together with R5 to form a carbon-hydrogen bond with the ring carbon to which it is attached;

its optical isomers and pharmaceutically-acceptable acid or base addition salt thereof;

which is effective for alleviation of said condition;

such a method-of-treating a living animal for alleviation of a condition treatable by a neuronal nicotinic receptor antagonist, comprising the step of administering to the living animal an amount of a compound selected from those of formula 1,

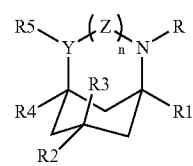

1 wherein
R is selected from the group consisting of hydrogen, straight or branched chain alkyl (C$_1$-C$_6$), straight or branched chain alkenyl (C$_2$-C$_6$), straight or branched chain alkynyl (C$_2$-C$_6$), aryl, substituted aryl, and arylalkyl;
R$^1$ is selected from the group consisting of straight or branched chain alkyl (C$_1$-C$_6$), straight or branched chain alkenyl (C$_2$-C$_6$), straight or branched chain alkynyl (C$_2$-C$_6$), aryl, substituted aryl, and arylalkyl;
R$^2$ through R$^5$ are independently selected from the group consisting of hydrogen, straight or branched chain alkyl (C$_1$-C$_6$), straight or branched chain alkenyl (C$_2$-C$_6$), straight or branched chain alkynyl (C$_2$-C$_6$), aryl, substituted aryl, and arylalkyl;
Z is CH$_2$;
N=0 or 1;
Y=CH;

or those compounds wherein R and R$^1$ combine to form a C$_3$-C$_5$ alkylene or alkenylene bridge U—V—W—X, resulting in the structure represented by formula 2,

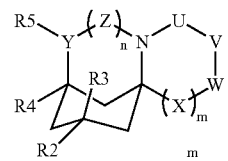

2 wherein X=CH$_2$;
m=0, 1, 2;

or those compounds wherein R and R$^1$ combine to form a C$_3$-C$_5$ alkylene or alkenylene bridge U—V—W—X, and ring members N and Y do not connect to form a bridge, resulting in the basic structure represented by formula 3,

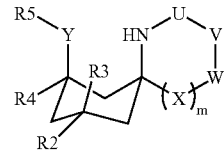

3 wherein ring member N is saturated and ring member Y is saturated or may combine together with R5 to form a carbon-hydrogen bond with the ring carbon to which it is attached;

its optical isomers and pharmaceutically-acceptable acid or base addition salt thereof;

which is effective for alleviation of said condition;

such a method-of-treating a living animal for alleviation of a condition treatable by a 5HT$_3$ antagonist selected from the group consisting of anxiety disorders, depressive disorders, Schizophrenia and treatment related psychosis, drug and alcohol abuse disorders, cognitive disorders, Alzheimer's disease, Parkinson's disease, cerebellar tremor, migraine, appetite disorders, inflammatory bowel syndrome (IBS), and emesis, comprising the step of administering to the living animal an amount of a compound selected from those of formula 1,

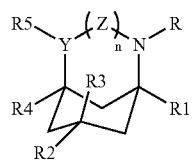

1 wherein

R is selected from the group consisting of hydrogen, straight or branched chain alkyl (C$_1$-C$_6$), straight or branched chain alkenyl (C$_2$-C$_6$), straight or branched chain alkynyl (C$_2$-C$_6$), aryl, substituted aryl, and arylalkyl;

R$^1$ is selected from the group consisting of straight or branched chain alkyl (C$_1$-C$_6$), straight or branched chain alkenyl (C$_2$-C$_6$), straight or branched chain alkynyl (C$_2$-C$_6$), aryl, substituted aryl, and arylalkyl;

R$^2$ through R$^5$ are independently selected from the group consisting of hydrogen, straight or branched chain alkyl (C$_1$-C$_6$), straight or branched chain alkenyl (C$_2$-C$_6$), straight or branched chain alkynyl (C$_2$-C$_6$), aryl, substituted aryl, and arylalkyl;

Z is CH$_2$;

N=0 or 1;

Y=CH;

or those compounds wherein R and R$^1$ combine to form a C$_3$-C$_5$ alkylene or alkenylene bridge U—V—W—X, resulting in the structure represented by formula 2,

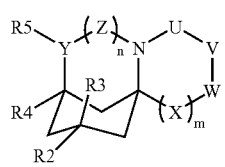

2 wherein X=CH$_2$;

m=0, 1, 2;

or those compounds wherein R and R$^1$ combine to form a C$_3$-C$_5$ alkylene or alkenylene bridge U—V—W—X, and ring members N and Y do not connect to form a bridge, resulting in the basic structure represented by formula 3,

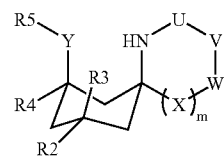

3 wherein ring member N is saturated and ring member Y is saturated or may combine together with R5 to form a carbon-hydrogen bond with the ring carbon to which it is attached;

its optical isomers and pharmaceutically-acceptable acid or base addition salt thereof;

which is effective for alleviation of said condition;

such a method-of-treating a living animal for alleviation of a condition treatable by a neuronal nicotinic receptor antagonist selected from the group consisting of Tourette's syndrome, anxiety disorders, Schizophrenia, drug abuse, nicotine abuse, cocaine abuse, dyskinesia (Morbus Huntington, L-DOPA-induced), attention deficit hyperactivity disorder (ADHD), Alzheimer's disease, Parkinson's disease, and pain, comprising the step of administering to the living animal an amount of a compound selected from those of formula 1,

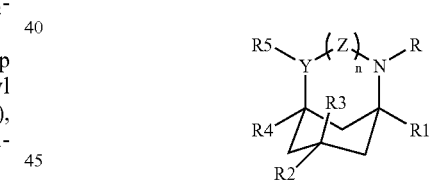

1 wherein

R is selected from the group consisting of hydrogen, straight or branched chain alkyl (C$_1$-C$_6$), straight or branched chain alkenyl (C$_2$-C$_6$), straight or branched chain alkynyl (C$_2$-C$_6$), aryl, substituted aryl, and arylalkyl;

R$^1$ is selected from the group consisting of straight or branched chain alkyl (C$_1$-C$_6$), straight or branched chain alkenyl (C$_2$-C$_6$), straight or branched chain alkynyl (C$_2$-C$_6$), aryl, substituted aryl, and arylalkyl;

R$^2$ through R$^5$ are independently selected from the group consisting of hydrogen, straight or branched chain alkyl (C$_1$-C$_6$), straight or branched chain alkenyl (C$_2$-C$_6$), straight or branched chain alkynyl (C$_2$-C$_6$), aryl, substituted aryl, and arylalkyl;

Z is CH$_2$;

N=0 or 1;

Y=CH;

or those compounds wherein R and R$^1$ combine to form a C$_3$-C$_5$ alkylene or alkenylene bridge U—V—W—X, resulting in the structure represented by formula 2,

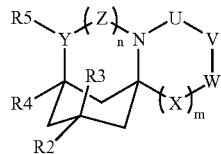

2 wherein X=CH$_2$;
m=0, 1, 2;

or those compounds wherein R and R$^1$ combine to form a C$_3$-C$_5$ alkylene or alkenylene bridge U—V—W—X, and ring members N and Y do not connect to form a bridge, resulting in the basic structure represented by formula 3,

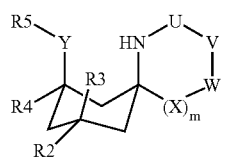

3 wherein ring member N is saturated and ring member Y is saturated or may combine together with R5 to form a carbon-hydrogen bond with the ring carbon to which it is attached;

its optical isomers and pharmaceutically-acceptable acid or base addition salt thereof;

which is effective for alleviation of said condition; and
such a pharmaceutical composition consisting of a compound selected from those of formula 1,

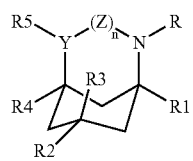

1 wherein

R is selected from the group consisting of hydrogen, straight or branched chain alkyl (C$_1$-C$_6$), straight or branched chain alkenyl (C$_2$-C$_6$), straight or branched chain alkynyl (C$_2$-C$_6$), aryl, substituted aryl, and arylalkyl;

R$^1$ is selected from the group consisting of straight or branched chain alkyl (C$_1$-C$_6$), straight or branched chain alkenyl (C$_2$-C$_6$), straight or branched chain alkynyl (C$_2$-C$_6$), aryl, substituted aryl, and arylalkyl;

R$^2$ through R$^5$ are independently selected from the group consisting of hydrogen, straight or branched chain alkyl (C$_1$-C$_6$), straight or branched chain alkenyl (C$_2$-C$_6$), straight or branched chain alkynyl (C$_2$-C$_6$), aryl, substituted aryl, and arylalkyl;

Z is CH$_2$;
N=0 or 1;
Y=CH;

or those compounds wherein R and R$^1$ combine to form a C$_3$-C$_5$ alkylene or alkenylene bridge U—V—W—X, resulting in the structure represented by formula 2,

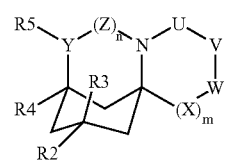

2 wherein X=CH$_2$;
m=0, 1, 2;

or those compounds wherein R and R$^1$ combine to form a C$_3$-C$_5$ alkylene or alkenylene bridge U—V—W—X, and ring members N and Y do not connect to form a bridge, resulting in the basic structure represented by formula 3,

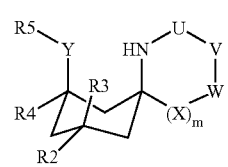

3 wherein ring member N is saturated and ring member Y is saturated or may combine together with R5 to form a carbon-hydrogen bond with the ring carbon to which it is attached;

its optical isomers and pharmaceutically-acceptable acid or base addition salt thereof;

in combination with one or more pharmaceutically-acceptable diluents, excipients, or carriers.

DETAILED DESCRIPTION OF THE INVENTION

Figure 1:
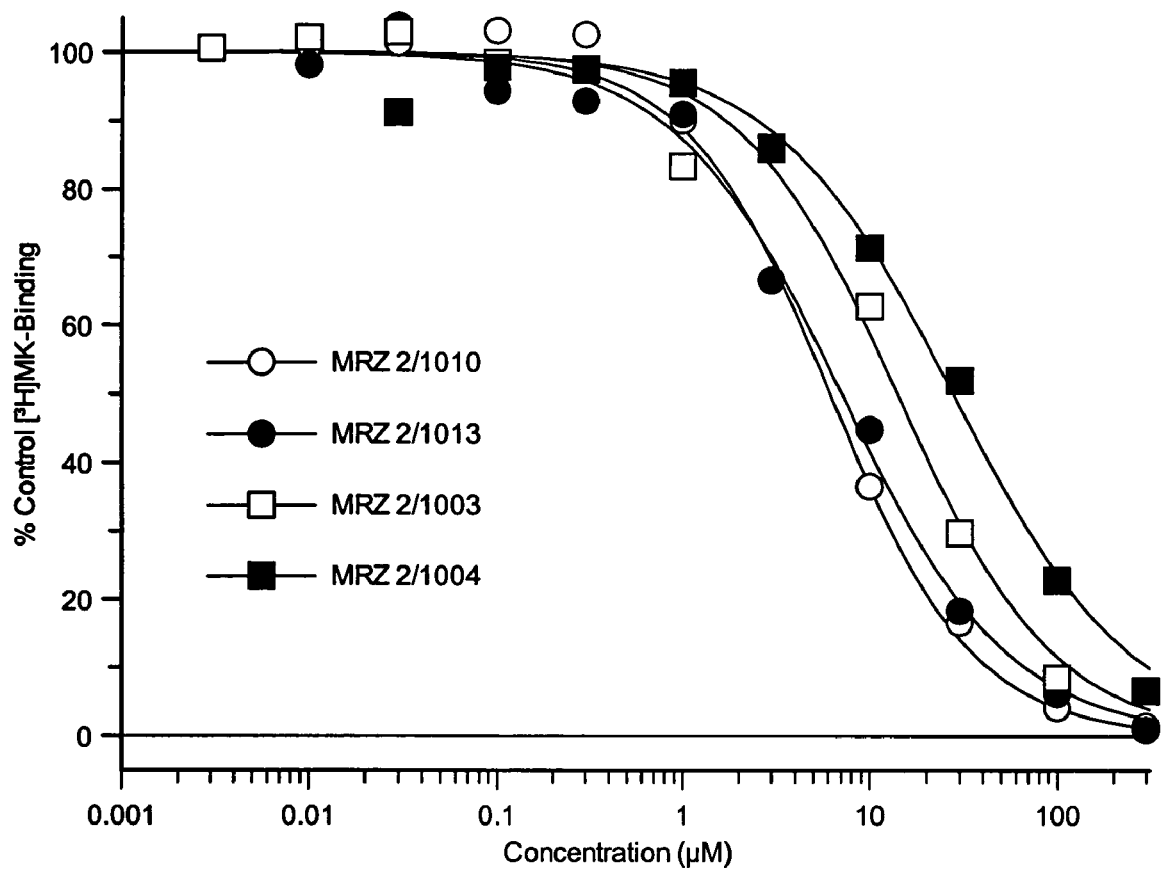
FIG. 1 shows $^3$H MK-Binding Results for representative compounds.

The following details and detailed Examples are given by way of illustration only, and are not to be construed as limiting.

Overall Synthetic Scheme and Table for the 6-Azabicyclo[3.2.1]octanes (Belonging to Structure of Formula 1 of the Summary):

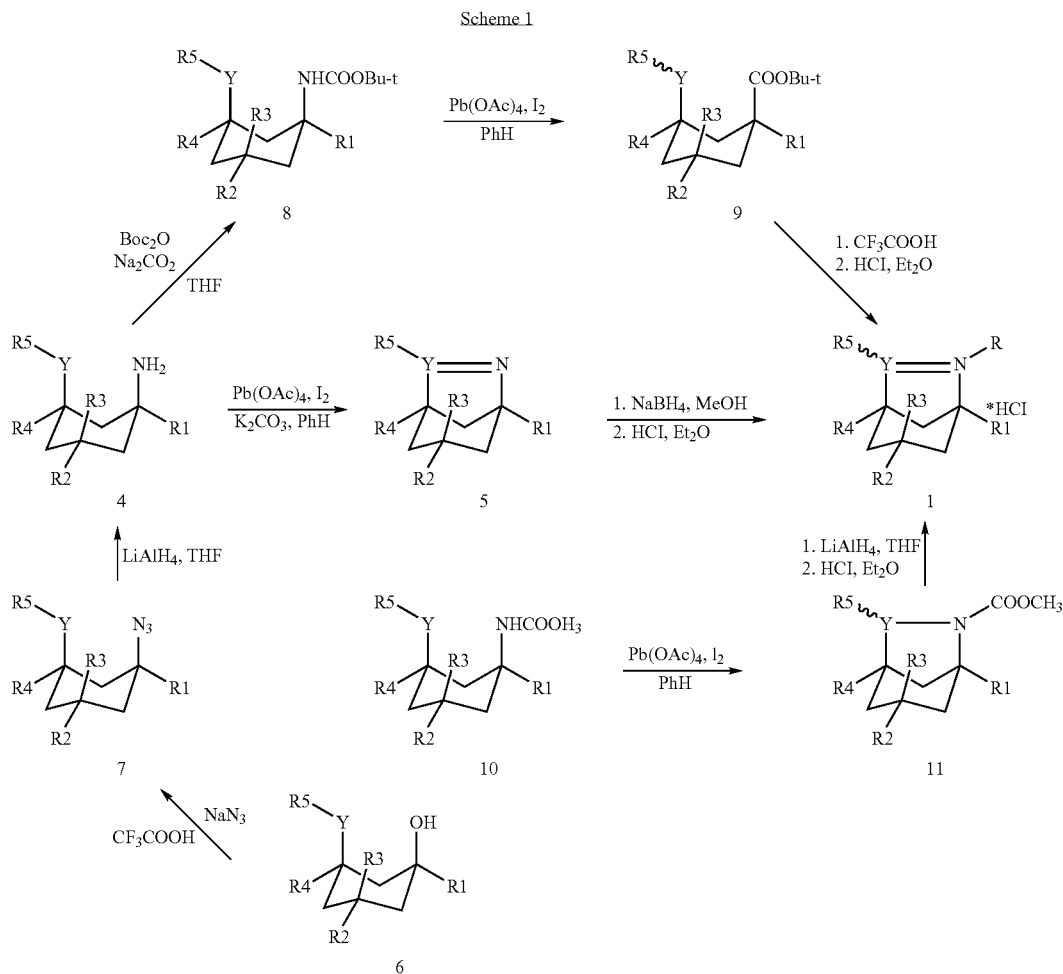

Scheme 1

TABLE 1

6-Azabicyclo[3.2.1]octanes 1-1 to 1-8

| MRZ number | number in synthetic descripition | R | $R^1$ | $R^2$ | $R^3$ | $R^4$ | $R^5$ | Y | n |
|---|---|---|---|---|---|---|---|---|---|
| 2011 | 1-1 | H | Me | Me | H | Me | H | CH | 0 |
| 2023 | 1-2 | H | Et | Me | H | Me | H | CH | 0 |
| 2007 | 1-3 | H | Me | Et | H | Me | H | CH | 0 |
| 2/1010 | 1-4 | H | Me | Me | Me | Me | H | CH | 0 |
| 2/1003 | 1-5 | Me | Me | Me | Me | Me | H | CH | 0 |
| 2022 | 1-6 | H | Et | Me | Me | Me | H | CH | 0 |
| 2029 | 1-7 | H | Me | Me | H | Me | Me | CH | 0 |
| 2028 | 1-8 | H | Me | Me | H | Me | Ph | CH | 0 |

EXAMPLE 1

1,exo-3,5-Trimethyl-6-azabicyclo[3.2.1]octane hydrochloride (1-1)

a) 1,exo-3,5-Trimethyl-6-azabicyclo[3.2.1]oct-6-ene (5-1)

A mixture of of 1,3,3, trans-5-tetramethylcyclohexanamine (4-1) (3.88 g, 25 mmol), $K_2CO_3$ (28 g, 0.2 mol) and lead tetraacetate (22.2 g, 50 mmol) in dry benzene (125 ml) was stirred for 3 h while boiling at reflux. Then it was cooled with ice water and filtered. The precipitate was washed with diethyl ether and the filtrate evaporated under reduced pressure. The oily residue was separated by column chromatography on silica gel (dichlorometane-iso-propyl alcohol, 20:1, 10:1). A fraction with Rf 0.7 (EtOAc) was collected to give after concentration under reduced pressure 1.0 g (26%) of imine 5-1 as an amber oil.

$^1$H NMR (CDCl$_3$, TMS) δ: 0.86 (3H, d, 6 Hz, 3-CH$_3$), 0.90-1.80 (7H, m, ring CH); 1.12 (3H, s, 1-CH$_3$); 1.34 (3H, s, 5-CH$_3$) and 7.36 ppm (1H, s, HC=).

b) 1,exo-3,5-Trimethyl-6-azabicyclo[3.2.1]octane hydrochloride (1-1)

A solution of imine 5-1 (0.8 g, 5.3 mmol) in MeOH (2 ml) was added dropwise to a suspension of sodium borohydride (0.4 g, 10.6 mmol) in MeOH (6 ml). The mixture was stirred at room temperature for 24 h, then 10 ml of 5% aqueous NaOH was added. The mixture was extracted with diethyl ether. The organic phase was washed with saturated aqueous NaCl and dried over NaOH pellets. The filtered solution was treated with dry HCl solution in diethyl ether, evaporated under reduced pressure and the residue was recrystallized from dry CH$_3$CN to give compound 1-1 as a colorless solid (0.33 g, 35%).

¹H NMR (CDCl₃, TMS) δ: 0.96 (3H, d, 6 Hz, 3-CH₃), 0.95-1.15 (1H, m, 2-CH); 1.11 (3H, s, 1-CH₃); 1.41 (1H, d, 12.4 Hz, 8-CH); 1.55-1.70 (1H, m, 2-CH); 1.57 (3H, s, 5-CH₃); 1.70-1.90 (2H, m, 4-CH and 8-CH); 2.00-2.30 (2H, m, 3-CH and 4-CH); 3.00-3.25 (2H, m, 7-CH₂) and 9.30-9.85 ppm (2H, br s, NH₂⁺).

EXAMPLE 2

5-Ethyl-1,exo-3-dimethyl-6-azabicyclo[3.2.1]octane hydrochloride (1-2)

a) 1-Azido-1-ethyl-3,3,trans-5-trimethylcyclohexane (7)

A cooled (~0° C.) mixture of 1-ethyl-3,3,trans-5-trimethylcyclohexanol (6) (3.3 g, 18.1 mmol), sodium azide (2.36 g, 36.3 mmol) and trifluoroacetic acid (10.7 ml) in chloroform (50 ml) was stirred for 24 h. Then it was made basic by diluted aqueous ammonia addition. The organic phase was separated, washed with water and dried over K₂CO₃. Filtration and solvent evaporation under reduced pressure gave an oily residue which was separated by flash chromatography on silica gel eluting with light petroleum ether to give azide 7 (2.0 g, 56%) as light colorless oil.

¹H NMR (CDCl₃, TMS) δ: 0.64 (1H, d, 14 Hz, ring CH); 0.85-2.15 (8H, m, ring CH and Et-CH₂); ); 0.90 (3H, d, 7 Hz, 5-CH₃); 0.92 (3H, s, 3-CH₃ₑq); 0.97 (3H, t, 7.5 Hz, Et-CH₃) and 1.10 ppm (3H, s, 3-CH₃ₐₓ).

b) 1-Ethyl-3,3,trans-5-trimethylcyclohexanamine (4-2)

Azide 7 (1.97 g, 10 mmol) solution in diethyl ether (10 ml) was added dropwise to a suspension of lithium aluminum hydride (1.13 g, 30 mmol) in diethyl ether (30 ml). The mixture was stirred for 20 h at room temperature. Then it was carefully quenched with 10% aqueous NaOH. The organic phase was separated and the aqueous phase extracted with diethyl ether. The combined organic phases were washed with saturated aqueous NaCl and dried over NaOH. Filtration and solvent evaporation under reduced pressure gave amine 4-2 (1.36 g, 80%) as an oil.

¹H NMR (CDCl₃, TMS) δ: 0.55-2.15 (9H, m, ring CH and Et-CH₂); 0.88 (3H, s, 3-CH₃ₑq); 0.89 (3H, d, 6.5 Hz, 5-CH₃); 0.89 (3H, t, 7 Hz, Et-CH₃) and 1.12 ppm (3H, s, 3-CH₃ₐₓ).

c) 5-Ethyl-1,exo-3-dimethyl-6-azabicyclo[3.2.1]octane hydrochloride (1-2)

Prepared in 30% yield from imine 5-2 according to procedure described in Example 1 b. Colorless solid.

¹H NMR (CDCl₃, TMS) δ: 0.95-1.15 (7H, m, ring CH, 3-CH and CH₃-Et); 1.12 (3H, s, 1-CH₃); 1.48 (1H, d, 13.6 Hz, 8-CH); 1.55-1.76 (3H, m, ring CH and CH₂-Et); 1.84-2.04 (2H, m, ring CH) and 2.04-2.28 (2H, m, 4,8-CH); 3.14 (2H, m, 7-CH₂) and 9.40 ppm (2H, br s, NH₂⁺).

d) 5-Ethyl-1,exo-3-dimethyl-6-azabicyclo[3.2.1]oct-6-ene (5-2)

Prepared in 32% yield from amine 4-2 according to procedure described in Example 1a. An oil.

¹H NMR (CDCl₃, TMS) δ: 0.82-0.95 (1H, m, ring CH); 0.91 (3H, d, 6 Hz, 3-CH₃), 0.94 (3H, t, 7.5 Hz, Et-CH₃); 1.15-1.75 (6H, m, ring CH); 1.15 (3H, s, 1-CH₃); 1.71 (2H, q, 7.5Hz, Et-CH₂) and 7.38 ppm (1H, s, HC=).

EXAMPLE 3 exo-3-Ethyl-1,5-dimethyl-6-azabicyclo[3.2.1]octane hydrochloride (1-3)

a) tert-Butyl trans-5-ethyl-1,3,3-trimethylcyclohexylcarbamate (8-1)

To a solution of 1,3,3-trimethyl-trans-5-ethylcyclohexanamine hydrochloride (4-3) (1.54 g, 7.5 mmol) in THF (20 ml) was added Na₂CO₃ (3.18 g, 30 mmol) and the mixture was stirred for 30 min. Then it was cooled with ice water, di-tert-butyl dicarbonate (1.7 g, 7.65 mmol) was added and stirring was continued for 20 h. Water was added and the mixture was twice extracted with diethyl ether. The combined extracts were washed with saturated aqueous NaCl, dried over MgSO₄ and evaporated. The solid residue was treated with hexane, filtered and washed with hexane to give carbamate 8-1. Additional amount of 8-1 was isolated after the filtrate was evaporated and treated with acetonitrile. Carbamate 8-1 (1.18 g, 57%) was obtained as a colorless solid with mp 70-71° C.

¹H NMR (CDCl₃, TMS) δ: 0.65-1.65 (7H, m, CH₂-Et and ring CH); 0.88 (3H, t, 6.5 Hz, CH₃-Et); 0.88 and 0.99 (both 3H, s, 3,3-CH₃); 1.42 (9H, s, t-Bu); 1.85 (1H, dq, 13.5 and 2.5 Hz, 6-CH_{eq}); 2.24 (1H, d, 14 Hz, 2-CH_{eq}) and 4.30 ppm (1H, br s, NH).

b) tert-Butyl exo-3-ethyl-1,5-dimethyl-6-azabicyclo[3.2.1]octane-6-carboxylate (9-1)

To a mixture of carbamate 8-1 (1.05 g, 3.85 mmol) and iodine (1.95 g, 7.7 mmol) in dry benzene (35 ml) was added lead tetraacetate (3.92 g, 8.85 mmol) in one portion. The mixture was stirred while boiling at reflux for 4 h then cooled with ice water and filtered. The precipitate was washed with diethyl ether and the filtrate carefully washed with saturated aqueous potassium metabisulfite followed by saturated aqueous NaHCO₃. The organic phase was washed with saturated aqueous NaCl, dried over MgSO₄ and evaporated. The residue was purified by flash chromatography on silica gel (light petroleum ether-ethyl acetate, 20:1) to give compound 9-1 (0.76 g, 73%) as a colorless oil.

¹H NMR (CDCl₃, TMS) δ: 0.86 (3H, t, 6.5 Hz, CH₃-Et); 1.00 (3H, s, 1-CH₃); 1.00-1.80 (7H, m, CH₂-Et and ring CH); 1.46 (12H, s, t-Bu and 5-CH₃); 1.95-2.45 (2H, m, ring-CH); 3.06 and 3.36 ppm (both 1H, d, 11 Hz, 7-CH₂).

c) exo-3-Ethyl-1,5-dimethyl-6-azabicyclo[3.2.1]octane hydrochloride (1-3)

Carbamate 9-1 (0.73 g, 2.7 mmol) was added to a solution of trifluoroacetic acid (3 ml) in dichloromethane (15 ml) and the mixture was stirred at room temperature for 10 h. The solution was evaporated under reduced pressure and the residue was treated with 10% aqueous NaOH (5 ml) and extracted with diethyl ether. The extract was washed with saturated aqueous NaCl and dried over NaOH. The filtered solution was treated with dry HCl solution in diethyl ether. The solvent was evaporated under reduced pressure and the residue was treated with dry acetonitrile to give amine hydrochloride 1-3 as colorless solid (0.34 g, 62%).

¹H NMR (CDCl₃, TMS) δ: 0.85-2.45 (9H, m, 2,4,8-CH₂, 3-CH and CH₂-Et); 0.90 (3h, t, 7 Hz, CH₃-Et); 1.12 (3H, s, 1-CH₃); 1.59 (3H, s, 5-CH₃); 3.13 (2H, t, 6 Hz, 7-CH₂) and 9.55 ppm (2H, br s, NH₂⁺).

EXAMPLE 4

1,3,3,5-Tetramethyl-6-azabicyclo [3.2.1]octane hydrochloride (1-4)

a) tert-Butyl 1,3,3,5,5-pentamethylcyclohexylcarbamate (8-2)

Prepared in 70% yield from 1,3,3,5,5-pentamethylcyclohexanamine hydrochloride (4-4) according to the procedure described in Example 3a. Purified by flash chromatography on silica gel (light petroleum ether-ethyl acetate, 20:1). A colorless oil.

$^1$H NMR (CDCl$_3$, TMS) δ: 0.87 (6H, s, 3,5-CH$_{3eq}$); 0.90-1.45 (4H, m, 4-CH$_2$ and 2,6-CH$_{ax}$); 1.12 (6H, s, 3,5-CH$_{3ax}$); 1.27 (3H, s, 1-CH$_3$); 1.42 (9H, s, t-Bu); 2.24 (2H, d, 15 Hz, 2,6-CH$_{eq}$) and 4.30 ppm (1H, br s, NH).

b) tert-Butyl 1,3,3,5-tetramethyl-6-azabicyclo[3.2.1] octane-6-carboxylate (9-2)

Prepared in 48% yield from carbamate 8-2 according to the procedure described in Example 3b. A colorless oil.

$^1$H NMR (CDCl$_3$, TMS) δ: 0.91, 0.94 and 0.99 (total 9H, all s, 1,3,3-CH$_3$); 0.80-1.75 (5H, m, ring CH); 1.34 and 1.52 (total 3H, both s, 5-CH$_3$); 1.41 and 1.44 (total 9H, both s, t-Bu); 1.91 and 2.09 (total 1H, both d, 14.5 Hz, 6-CH); 3.00 and 3.28 (one rotamer); and 3.03 and 3.33 (another rotamer; total 2H, all dd, 11 and 2 Hz, 7-CH$_2$).

c) 1,3,3,5-Tetramethyl-6-azabicyclo [3.2.1]octane hydrochloride (1-4)

Prepared in 68% yield from carbamate 9-2 according to the procedure described in Example 3c. Colorless solid.

$^1$H NMR (CDCl$_3$, TMS) δ: 1.00, 1.13 and 1.29 (total 9H, s, 1,3,3-CH$_3$); 1.25-1.65 (4H, m, 2-CH$_2$ and 4,8-CH); 1.64 (3H, s, 5-CH$_3$); 1.81 (1H, dt, 12.4 and 2.3 Hz, 4-CH); 2.21 (1H, d, 14.5 Hz, 8-CH); 3.10-3.40 (2H, m, 7-CH$_2$); 9.10 and 9.90 ppm (total 2H, both br s, NH$_2^+$).

EXAMPLE 5

1,3,3,5,6-Pentamethyl-6-azabicyclo [3.2.1]octane hydrochloride (1-5)

a) Methyl 1,3,3,5-tetramethyl-6-azabicyclo[3.2.1] octane-6-carboxylate (11)

Prepared in 50% yield from methyl 1,3,3,5,5-pentamethylcyclohexylcarbamate (10) according to the procedure described in Example 3b. A colorless oil.

$^1$H NMR (CDCl$_3$, TMS) δ: 0.87 and 0.96 (total 9H, both s, 1,3,3-CH$_3$); 1.00-1.70 (4H, m, 2-CH$_2$ and 4,8-CH); 1.33 and 1.46 (total 3H, both s, 1-CH$_3$); 1.70-1.20 (2H, m, 4,8-CH); 3.04 and 3.34 (major rotamer) and 3.10 and 3.39 (minor rotamer; total 2H, all dd, 11.5 and 1.5 Hz, 7-CH$_2$); 3.59 (major) and 3.64 (total 3H, both s, OCH$_3$).

b) 1,3,3,5,6-Pentamethyl-6-azabicyclo [3.2.1]octane hydrochloride (1-5)

A solution of carbamate 11 (1.0 g, 4.44 mmol) in diethyl ether (10 ml) was added to a suspension of lithium aluminum hydride (0.34 g, 9 mmol) in diethyl ether (25 ml). The mixture was stirred for 20 h at room temperature. Then it was cooled with ice water and carefully quenched with 10% aqueous NaOH. The organic phase was separated and the aqueous phase extracted with diethyl ether. The combined organic phases were washed with saturated aqueous NaCl and dried over NaOH. Filtered solution was treated with an excess amount of dry HCl solution in diethyl ether. The solvent was evaporated under reduced pressure and the residue was treated with dry acetonitrile and diethyl ether (2:1), and cooled in refrigerator for 24 h. The precipitate was filtered and washed with diethyl ether to give amine hydrochloride 1-5 (0.25 g, 26%) as a colorless solid.

$^1$H NMR (CDCl$_3$, TMS) δ: 1.03, 1.09, 1.16 and 1.22 (total 9H, all s, 1,3,3-CH$_3$); 1.44 (3H, s, 5-CH$_3$); 1.50-2.50 (6H, m, 2, 4, 8-CH$_2$); 2.73 (d, 5 Hz) and 2.80 (total 3H, d, 5.5 Hz, N-CH$_3$); 2.55 (m) and 2.94 (total 1H, dd, 12 and 6 Hz, 7-CH); 3.73 (dd, 12 and 8.5 Hz) and 4.07 (total 1H, dd, 13 and 7 Hz, 7-CH); 9.50 and 10.80 ppm (total 1H, br s, NH$^+$).

EXAMPLE 6

5-Ethyl-1,3,3-trimethyl-6-azabicyclo[3.2.1]octane hydrochloride (1-6)

a) 5-Ethyl-1,3,3-trimethyl-6-azabicyclo[3.2.1]oct-6-ene (5-3)

Prepared in 28% yield from 1-ethyl-3,3,5,5-tetramethylcyclohexanamine (4-5) according to the procedure described in Example 1a. An oil.

$^1$H NMR (CDCl$_3$, TMS) δ: 0.93 (3H, s, 3-CH$_3$); 0.94 (3H, t, 7.4 Hz, Et-CH$_3$); 0.98 (3H, s, 3-CH$_3$); 1.15 (3H, s, 1-CH$_3$); 1.20-1.50 (5H, m, ring CH): 1.57 (1H, dt, 12.4 and 2 Hz, ring CH); 1.69 (2H, dq, 7.5 and 2.8 Hz, Et-CH$_2$) and 7.47 ppm (1H, s, HC=).

b) 5-Ethyl-1,3,3-trimethyl-6-azabicyclo[3.2.1]octane hydrochloride (1-6)

Prepared in 33% yield from imine 5-3 according to the procedure described in Example 1b.
Colorless solid.

$^1$H NMR (CDCl$_3$, TMS) δ: 1.01 (3H, s, 3-CH$_3$); 1.03 (3H, t, 7.5 Hz, CH$_3$-Et); 1.13 and 1.31 (both 3H, s, 1,3-CH$_3$); 1.25-1.35 (1H, m, ring CH); 1.35-1.65 (4H, m, CH$_2$-Et and ring CH); 1.69 (1H, d, 12 Hz, 2-CH); 1.92-2.12 (2H, m, 4,8-CH); 3.05-3.45 (2H, m, 7-CH$_2$): 9.05 and 9.65 ppm (both 1H, br s, NH$_2^+$).

EXAMPLE 7

1, exo-3,5, exo,endo-7-Tetramethyl-6-azabicyclo[3.2.1]octane hydrochloride (1-7)

a) tert-Butyl cis-3-ethyl-1,3,trans-5-trimethylcyclohexylcarbamate (8-3)

Prepared in 81% yield from 1,3,5-trimethyl-cis-3-ethyl-cyclohexanamine hydrochloride (4-6) according to the procedure described in Example 3a. Purified by flash chromatography on silica gel (light petroleum ether-ethyl acetate, 20:1). A colorless oil.

$^1$H NMR (CDCl$_3$, TMS) δ: 0.63 (1H, d, 12.5 Hz, ring CH); 0.70-0.90 (1H, m, ring CH); 0.79 (3H, t, 7.5 Hz, CH$_3$-Et); 0.86 (3H, d, 6.4 Hz, 5-CH$_3$); 1.28 (3H, s, 3-CH$_3$); 1.25-1.85 (6H, m, ring CH and CH$_2$-Et); 1.41 (9H, s, t-Bu); 1.52 (3H, s, 1-CH$_3$); 2.35 (1H, d, 12.5 Hz, 2-CH) and 4.31 ppm (1H, br s, NH).

tert-Butyl 1, exo-3,5, exo,endo-7-tetramethyl 6-azabicyclo[3.2.1]octane-6-carboxylate (9-3)

Prepared in 57% yield from carbamate 8-3 according to the procedure described in Example 3b. A colorless oil.

$^1$H NMR (CDCl$_3$, TMS) δ: 0.60-1.85 (6H, m, ring CH); 0.85-1.15 (6H, m, 1,3-CH$_3$); 1.35-1.55 (6H, m, 5,7-CH$_3$); 1.45 (9H, s, t-Bu); 2.06 and 2.27 (total 1H, m, ring CH); 3.36 and 3.51 ppm (total 1H, m, 7-CH).

1, exo-3,5, exo,endo-7-Tetramethyl-6-azabicyclo[3.2.1]octane hydrochloride (1-7)

Prepared in 70% yield from carbamate 9-3 according to the procedure described in Example 3c. A colorless solid.

$^1$H NMR (CDCl$_3$, TMS) δ: 0.96 (3H, d, 5.8 Hz, 3-CH$_3$); 1.00 (3H, s, 1-CH$_3$); 1.00-1.15 (1H, m, 2-CH); 1.36 (1H, d, 12 Hz, 8-CH); 1.43 (3H, d, 7.4 Hz, 7-CH$_3$); 1.55-1.75 (2H, m, 2-CH and 4-CH); 1.62 (3H, s, 5-CH$_3$); 1.90 (1H, d, 12.6 Hz, 8-CH); 2.15-2.35 (2H, m, 3-CH and 4-CH); 3.65 (1H, m, 7-CH); 9.00 and 9.95 ppm (total 2H, both br s, NH$_2^+$).

EXAMPLE 8

1, exo-3,5-Trimethyl-exo,endo-7-phenyl-6-azabicyclo[3.2.1]octane hydrochloride (1-8)

a) 3-Benzyl-3,5-dimethylcyclohexanone (13)

To a cooled (−20° C.) 1M benzylmagnesium bromide solution in diethyl ether (50 ml) under argon was added CuCl (0.52 g, 5.3 mmol) and the mixture was stirred for 5 min. Then a solution of 3,5-dimethyl-2-cyclohexen-1-one (12) (4.4 g, 35.1 mmol) in diethyl ether (15 ml) was added dropwise keeping the temperature below −10° C. The mixture was stirred for 2 h and quenched with 10% aqueous acetic acid (40 ml). The organic layer was separated, washed with water, saturated aqueous NaHCO$_3$ and saturated aqueous NaCl, and dried over MgSO$_4$. Filtration and concentration in vacuo afforded oily residue what was separated by flash chromatography on silica gel (light petroleum ether-ethyl acetate, 10:1). Cyclohexanone 13 (4.0 g, 53%) was obtained as a colorless oil.

$^1$H NMR (CDCl$_3$, TMS) δ: 0.92 (3H, s, 3-CH$_3$); 1.06 (3H, d, 6 Hz, 5-CH$_3$), 1.10-2.45 (7H, m, ring CH); 2.42 and 2.56 (total 2H, both d, 13 Hz, CH$_2$Ph) and 7.05-7.35 ppm (5H, m, Ph).

b) cis-3-Benzyl-1,3,trans-5-trimethylcyclohexanol (14)

A solution of ketone 13 (3.9 g, 18.1 mmol) in diethyl ether (10 ml) was added dropwise to 1M MeMgI in diethyl ether (40 ml). The mixture was stirred for 1 h at room temperature. Etheral extract obtained after traditional workup for Grignard reactions was dried over Na$_2$SO$_4$, filtered and evaporated to give an oily residue what was purified by flash chromatography on silica gel (light petroleum ether-ethyl acetate). Cyclohexanol 14 (3.2 g, 76%) was obtained as a colorless oil.

$^1$H NMR (CDCl$_3$, TMS) δ: 0.75 (3H, s, 3-CH$_3$); 0.95-1.25 (3H, m, ring CH); 0.92 (3H, d, 6.6 Hz, 5-CH$_3$), 1.23 (3H, s, 1-CH$_3$); 1.45-1.75 (3H, m, ring CH); 2.05-2.25 (1H, m, 5-CH); 2.77 and 3.04 (both 1H, d, 13 Hz, CH$_2$Ph) and 7.05-7.35 ppm (5H, m, aryl CH).

c) N-(cis-3-Benzyl-1,3,trans-5-trimethylcyclohexyl)-2-chloroacetamide (15)

Sulfuric acid (2.1 ml, 3.83 g, 39 mmol) was added dropwise to a stirred solution of cyclohexanol 14 (3.0 g, 13 mmol) and chloroacetonitrile (4.0 g, 52 mmol) in acetic acid (2.1 ml) while cooling with ice water. The mixture was stirred for 24 h at room temperature then poured into ice water (10 ml). The mixture was neutralised with 20% aqueous NaOH and extracted with diethyl ether (3×15 ml). The combined organic phases were washed with saturated aqueous NaCl and dried over MgSO$_4$. The extract was filtered and the solvent evaporated. The residue was purified by flash chromatography on silica gel eluting with a mixture of light petroleum ether and ethyl acetate (10:1) to give amide 15 (1.32 g, 33%) as a colorless oil.

$^1$H NMR (CDCl$_3$, TMS) δ: 0.73 (3H, s, 3-CH$_3$); 0.90-1.40 (3H, m, ring CH); 0.98 (3H, d, 6.6 Hz, 5-CH$_3$), 1.42 (3H, s, 1-CH$_3$); 1.63 (1H, m, ring CH); 1.80-2.05 (1H, m, 5-CH); 2.12 (1H, dq, 13.8 and 3 Hz, 6-CH); 2.33 (1H, d, 12.7 Hz, CH$_2$Ph); 2.51 (1H, dt, 15 and 2.2 Hz, 2-CH); 3.17 (1H, d, 12.7 Hz, CH$_2$Ph); 3.95 and 3.96 (total 2H, both s, CH$_2$CO); 6.52 (1H, br s, NH) and 7.00-7.35 ppm (5H, m, aryl CH).

d) cis-3-Benzyl-1,3,trans-5-trimethylcyclohexanamine hydrochloride (4-7)

A solution of amide 15 (0.62 g, 2 mmol) and thiourea (0.18 g, 2.4 mmol) in a mixture of ethanol (5 ml) and acetic acid (1 ml) was refluxed for 10 h. The reaction mixture was cooled to room temperature and 20 ml of 10% aqueous NaOH was added while stirring. The resulting mixture was extracted with diethyl ether (3×10 ml). The combined extracts were washed with saturated aqueous NaCl, dried over NaOH, filtered and treated with dry HCl solution in diethyl ether. The solvent was evaporated under reduced pressure and the residue treated with dry diethyl ether to give amine hydrochloride 4-7 (0.33 g, 35%) as a colorless solid.

$^1$H NMR (CDCl$_3$, TMS) δ: 0.68 (3H, d, 6.5 Hz, 5-CH$_3$); 0.70-1.30 (3H, m, ring CH); 0.73 (3H, s, 3-CH$_3$); 1.28 (3H, s, 1-CH$_3$); 1.50 (1H, d, 15.4 Hz, ring CH); 1.60-1.85 (1H, m, ring CH); 2.05 (1H, d, 16 Hz, ring CH); 2.15-2.50 (1H, m, 5-CH); 2.47 and 3.33 (both 1H, d, 12.8 Hz, CH$_2$Ph); 7.00-7.35 (5H, m, aryl CH) and 8.42 ppm (3H, br s, NH$_3^+$).

e) 1, exo-3,5-Trimethyl-7-phenyl-6-azabicyclo[3.2.1]oct-6-ene (5-4)

Prepared in 40% yield from free amine 4-7 according to the procedure described in Example 1a. An oil.

$^1$H NMR (CDCl$_3$, TMS) δ: 0.94 (3H, d, 6.6 Hz, 3-CH$_3$); 0.90-1.15 (2H, m, ring CH): 1.26 (3H, s, 1-CH$_3$); 1.30-1.90 (5H, m, ring CH); 1.43 (3H, s, 5-CH$_3$) and 7.30-7.65 ppm (5H, m, aryl CH).

f) 1,exo-3,5-Trimethyl-exo,endo-7-phenyl-6-azabicyclo[3.2.1]octane hydrochloride (1-8)

Prepared in 33% yield from imine 5-4 according to the procedure described in Example 1b.

Colorless solid.

$^1$H NMR (CDCl$_3$, TMS) δ: 0.75-1.95 (4H, m, ring CH); 0.86 (3H, d, 5.8 Hz, 3-CH$_3$); 1.20 (3H, s, 1-CH$_3$; 1.56 (3H, s, 5-CH$_3$); 1.99 (1H, d, 14.4 Hz, 8-CH); 2.05-2.15 (1H, m, ring CH); 2.20-2.30 (1H, m, ring CH); 4.57 (1H, m, 7-CH); 7.24 and 7.65 (total 5H, both br s, Ph); 9.15 and 10.40 ppm (total 2H, both br s, $NH_2^+$).

Overall synthetic scheme and table for 6-Azabicyclo[3.2.1]nonanes (belonging to the structure of formula 1 of the Summary).

from a fraction with Rf 0.7-0.8 (Hexanes-EtOAc, 2:1) separated after the synthesis of compound 15, Example 8c) in a mixture of acetonitrile (16 ml), tetrachloromethane (16 ml) and water (23 ml) was added sodium periodate (10.5 g, 49 mmol) and ruthenium dioxide (7 mg, 0.06 mmol). The mixture was stirred at room temperature for 72 h, then it was filtered and the filter cake was washed with dichloromethane. The organic phase of the filtrate was separated and the aqueous phase was extracted with dichloromethane. The combined organic phases were dried over $CaCl_2$, filtered and evaporated. The residue was purified by flash chromatography on silica gel eluting with chloroform to give acid 16 (0.55 g, 41%) as an oil.

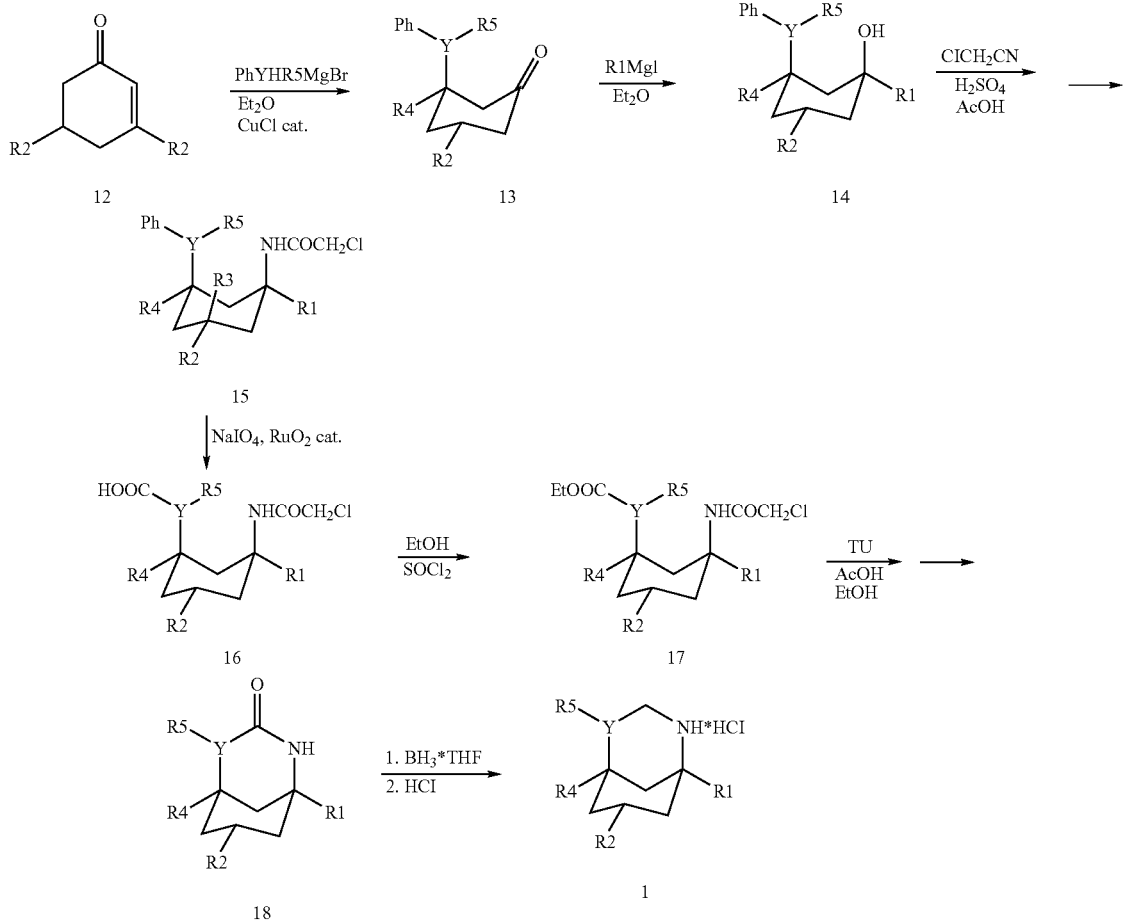

Scheme 2

TABLE 2

6-Azabicyclo[3.2.1]nonane 1-9

| MRZ number | number in synthetic descripition | R | $R^1$ | $R^2$ | $R^3$ | $R^4$ | $R^5$ | Y | n |
|---|---|---|---|---|---|---|---|---|---|
| 2046 | 1-9 | H | Me | Me | H | Me | H | CH | 1 |

EXAMPLE 9

1,5,exo-7-Trimethyl-2-azabicyclo[3.3.1]nonane hydrochloride (1-9)

a) 2-{cis-3-[(2-Chloroacetyl)amino]-1,3,trans-5-trimethylcyclohexyl}acetic acid (16)

To a solution of 1.5 g (4.9 mmol) of N-(cis-3-Benzyl-1,3,trans-5-trimethylcyclohexyl)-2-chloroacetamide (obtained $^1$H NMR (DMSO-$d_6$, TMS) δ: 0.8-2.6 (7H, m, ring CH); 0.84 and 0.85 (total 3H, d, 6 Hz, 5-$CH_3$); 0.92 and 1.01 (total 3H, s, 1-$CH_3$); 1.21 and 1.22 (total 3H, s, 3-$CH_3$); 2.19 and 2.39 (total 2H, both d, 13.5 Hz, $CH_2CO$); 3.97 ppm (2H, s, $CH_2Cl$); 7.57 and 7.70 (total 1H, both br s, NH) and 12.05 ppm (1H, br s, COOH).

b) Ethyl 2-{cis-3-[(2-chloroacetyl)amino]-1,3,trans-5-trimethylcyclohexyl}acetate (17)

Thionyl chloride (0.73 ml, 10 mmol) was added dropwise to a solution of acid 16 (0.55 g, 1.99 mmol) in dry ethanol (5 ml), while cooling with ice water. The resulting solution was stirred for 15 h at room temperature then evaporated under reduced pressure. The residue was purified by flash chromatography on silica gel eluting with a mixture of light petroleum ether and ethyl acetate (6:1) to give ethyl ester 17 (0.32 g, 54%) as an oil.

$^1$H NMR (CDCl$_3$, TMS) δ: 0.7-1.6 (4H, m, ring CH); 0.88-0.94 (3H, m, 5-CH$_3$); 1.04 and 1.14 (total 3H, s, 1-CH$_3$); 1.25 (2H, t, 7 Hz, CH$_3$-ethyl); 1.35 and 1.36 (total 3H, s, 3-CH$_3$); 1.6-1.8 (1H, m, 5-CH); 2.05-2.35 (2H, m, ring CH); 2.16 and 2.79 (total 2H, d, 13 Hz, CH$_2$CO); 3.92 and 3.95 (total 2H, s, CH$_2$Cl); 4.12 (2H, q, 7 Hz, CH$_2$O); 6.42 and 7.28 ppm (total 1H, br s, NH).

c) 1,5,exo-7-Trimethyl-2-azabicyclo[3.3.1]nonan-3-one (18)

A solution of ethyl ester 17 (0.32 g, 1.07 mmol) and thiourea (0.098 g, 1.3 mmol) in a mixture of ethanol (5 ml) and acetic acid (1.2 ml) was refluxed for 20 h. The reaction mixture was cooled to room temperature and the solvents evaporated. 10% aqueous NaOH was added and the mixture was extracted with chloroform (3×10 ml). The combined organic extracts were dried over CaCl$_2$, filtered and evaporated. The residue was purified by flash chromatography on silica gel eluting with a mixture of light petroleum ether and ethyl acetate (6:1, 3:1). A fraction with Rf 0.4 (Hexane-EtOAc, 2:1) was collected to give lactam 18 (0.12 g, 39%) as a colorless solid with mp 176-177° C.

$^1$H NMR (CDCl$_3$, TMS) δ: 0.89 (3H, d, 5.8 Hz, 7-CH$_3$); 0.75-1.05 (3H, m, ring CH); 0.99 (3H, s, 5-CH$_3$); 1.20 (3H, s, 1-CH$_3$); 1.24-1.36 (1H, m, ring CH); 1.45-1.60 (2H, m, ring CH); 1.60-1.84 (1H, m, 7-CH); 2.14 (2H, s, 4-CH$_2$) and 5.40 ppm (1H, br s, NH).

d) 1,5,7-Trimethyl-2-azabicyclo[3.3.1]nonane hydrochloride (1-9)

1 M Borane solution in tetrahydrofuran (2 ml, 2 mmol) was added to a solution of lactam 18 (0.07 g, 0.385 mmol) in tetrahydrofuran (2 ml) and refluxed for 15 h. The mixture was cooled to room temperature and made acidic by addition of conc. aqueous HCl. Solvents were evaporated under reduced pressure and hexane (10 ml) and 20% aqueous NaOH (10 ml) were added to the residue. The organic phase was separated and the aqueous phase was extracted with hexane (2×5 ml). The combined organic phases were washed with saturated aqueous NaCl (10 ml) and dried over NaOH. The extract was filtered and dry HCl solution in diethyl ether was added. The solvent was evaporated and the residue was treated with diethyl ether (5 ml). The precipitate was collected on a filter to give amine hydrochloride 1-9 (0.02 g, 25%) as a colorless solid.

$^1$H NMR (CDCl$_3$, TMS) δ: 0.80-1.85 (7H, m, ring CH); 0.88 (3H, d, 6.5 Hz, 7-CH$_3$); 0.96 (3H, s, 5-CH$_3$); 1.50 (3H, s, 1-CH$_3$); 2.10-2.40 (2H, m, 7-CH and 8-CH); 3.15-3.35 and 3.30-3.55 (both 1H, m, 3-CH$_2$); 9.15 and 9.55 ppm (both 1H, br s, NH$_2^+$).

Overall Synthetic Scheme and Table for 1-Azaspiro Compounds (Belonging to the Structure of Formula 3 of the Summary).

Scheme 3

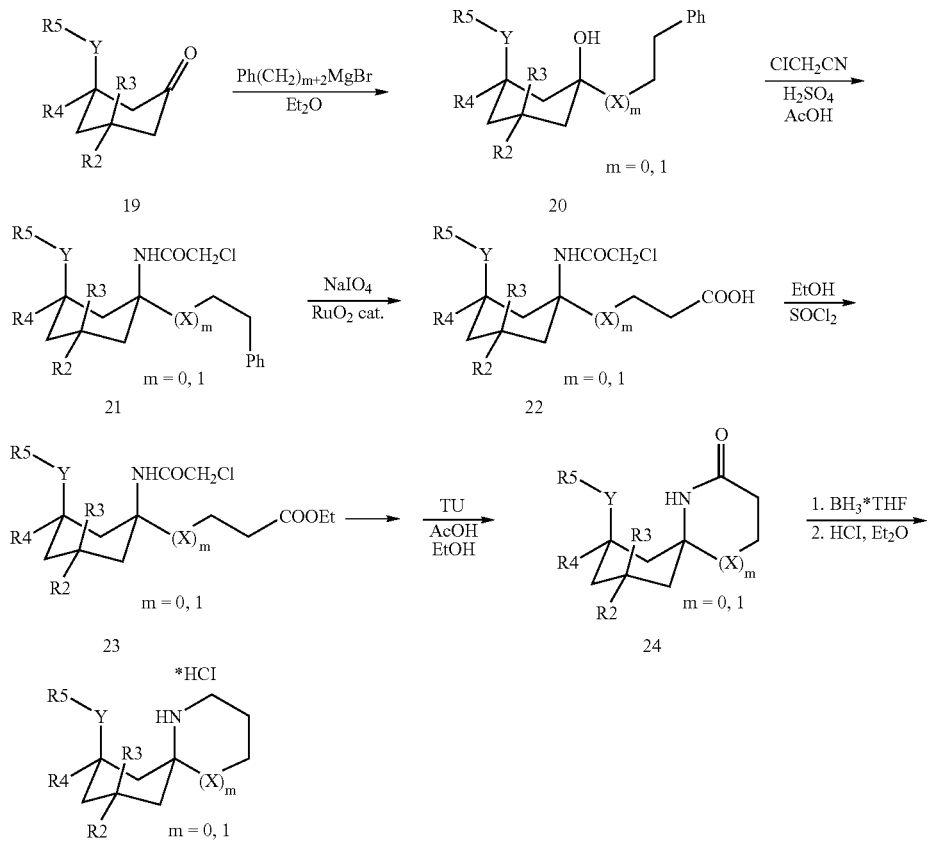

TABLE 3

| MRZ number | number in synthetic description | R | R¹ | R² | R³ | R⁴ | R⁵ | Y | n |
|---|---|---|---|---|---|---|---|---|---|
| 2/1004 | 3-1 | —(CH₂)₃—, (m = 0) | Me | Me | Me | H | CH₂ | — |
| 2/1013 | 3-2 | —(CH₂)₄—, (m = 1) | Me | Me | Me | H | CH₂ | — |

EXAMPLE 10

7,7,9,9-Tetramethyl-1-azaspiro[4.5]decane hydrochloride (3-1)

a) 3,3,5,5-Tetramethyl-1-(2-phenylethyl)cyclohexanol (20-1)

A solution of 3,3,5,5-pentamethylcyclohexanone (19) (1.54 g, 10 mmol) in diethyl ether (10 ml) was added to 0.85 M solution of phenylethylmagnesium bromide in diethyl ether (25 ml, 20 mmol), while cooling with an ice bath. The resulting mixture was stirred for 0.5 h and saturated aqueous NH₄Cl (30 ml) was added thoroughly. The organic phase was separated and the aqueous phase was washed with diethyl ether (2×20 ml). The combined organic phases were washed with saturated aqueous NaCl solution (20 ml) and dried over MgSO₄. Filtration and evaporation of the solution gave a residue what was purified by flash chromatography on silica gel eluting with a mixture of light petroleum ether and ethyl acetate (10:1) to give cyclohexanol 20-1 (2.1 g, 82%) as an oil.

$^1$H-NMR (CDCl₃, TMS) δ: 0.91 (6H, s, 3,5-CH₃); 1.23 (6H, s, 3,5-CH₃); 1.0-1.6 (7H, m, ring protons and OH); 1.6-1.8 (2H, m, PhCH₂CH₂); 2.6-2.8 (2H, m, PhCH₂CH₂) and 7.0-7.4 ppm. (5H, m, Ph).

b) 2-Chloro-N-[3,3,5,5-tetramethyl-1-(2-phenylethyl)cyclohexyl]acetamide (21-1)

Prepared in 96% yield from cyclohexanol 20-1 according to the procedure described in Example 8c. A colorless oil.

$^1$H-NMR (CDCl₃, TMS) δ: 0.93 (6H, s, 3,5-CH₃); 1.17 (6H, s, 3,5-CH₃); 1.0-1.5 (4H, m, 4-CH₂, 2,6-CH); 2.0-2.2 (2H, m, PhCH₂CH₂); 2.24 (2H, d, 14 Hz, 2,6-CH); 2.5-2.6 (2H, m, PhCH₂CH₂); 3.90 (2H, s, CH₂Cl); 6.60 (1H, br s, NH) and 7.1-7.3 ppm (5H, m, Ph).

c) 3-{1-[(2-Chloroacetyl)amino]-3,3,5,5-tetramethylcyclohexyl}propanoic acid (22-1)

Prepared 53% yield from amide 21-1 in according to the procedure described in Example 9a. A colorless crystals with mp 130-131° C.

$^1$H-NMR (CDCl₃, TMS) δ: 0.92 (6H, s, 3,5-CH₃); 1.17 (6H, s, 3,5-CH₃); 1.0-1.5 (4H, m, 4-CH₂, 2,6-CH,); 2.0-2.4 (6H, m, OCCH₂CH₂, 2,6-CH); 3.97 (2H, s, CH₂Cl) and 6.6 ppm (1H, br s, NH);

d) Ethyl 3-{1-[(2-chloroacetyl)amino]-3,3,5,5-tetramethylcyclohexyl}propanoate (23-1)

Prepared in 82% yield from acid 22-1 according to the procedure described in Example 9b. An oil.

$^1$H-NMR (CDCl₃, TMS) δ: 0.91 (6H, s, 3,5-CH₃); 1.14 (6H, s, 3,5-CH₃); 1.25 (3H, t, 7 Hz, CH₃CH₂O); 0.8-1.6 (4H, m, 4-CH₂, 2,6-CH); 2.0-2.4 (6H, m, OCCH₂CH₂, 2,6-CH); 3.95 (2H, s, CH₂Cl); 4.11 (2H, q, 7 Hz, CH₃CH₂O) and 6.50 ppm (1H, br s, NH).

e) 7,7,9,9-Tetramethyl-1-azaspiro[4.5]decan-2-one (24-1)

Prepared in 54% yield from ester 23-1 according to the procedure described in Example 9c. A colorless solid with mp 158-160° C.

$^1$H-NMR (CDCl₃, TMS) δ: 1.01 (12H, s, 7,9-CH₃); 1.19 (1H, d, 14 Hz, 8-CH); 1.27 (1H, d, 14 Hz, 8-CH); 1.45 (4H, s, 6,10-CH₂); 2.02 (2H, t, 7.5 Hz, 4-CH₂); 2.36 (2H, t, 7.5 Hz, 3-CH₂) and 5.8 ppm (1H, br s, NH).

f) 7,7,9,9-Tetramethyl-1-azaspiro[4.5]decane hydrochloride (3-1)

Prepared in 76% yield from spirolactam 24-1 according to the procedure described in Example 9d. Colorless solid.

$^1$H-NMR (CDCl₃, TMS) δ: 1.01 (6H, s, 7,9-CH₃); 1.08 (6H, s, 7,9-CH₃); 1.23 (1H, d, 14 Hz, 8-CH); 1.35 (1H, d, 14 Hz, 8-CH); 1.8 (4H, br s, 6,10-CH₂); 2.0-2.2 (4H, m, 3,4-CH₂); 3.3 (2H, br s, 2-CH₂) and 9.4 ppm (2H, br s, NH₂⁺).

EXAMPLE 11

8,8,10,10-Tetramethyl-1-azaspiro[5.5]undecane hydrochloride (3-2)

a) 3,3,5,5-Tetramethyl-1-(3-phenylpropyl)cyclohexanol (20-2)

Prepared in 90% yield from ketone 19 according to the procedure described in Example 10a. A colorless oil.

$^1$H-NMR (CDCl₃, TMS) δ: 0.86 (6H, s, 3,5-CH₃); 1.19 (6H, s, 3,5-CH₃); 1.0-1.8 (11H, m, ring protons, OH and PhCH₂CH₂CH₂); 2.60 (2H, t, 7.5 Hz, PhCH₂CH₂CH₂) and 7.1-7.4 ppm (5H, m, Ph).

b) 2-Chloro-N-[3,3,5,5-tetramethyl-1-(3-phenylpropyl)cyclohexyl]acetamide (21-2)

Prepared in 37% yield from cyclohexanol 20-2 according to the procedure described in Example 8c. Colorless solid with mp 83-85° C.

$^1$H-NMR (CDCl₃, TMS) δ: 0.89 (6H, s, 3,5-CH₃); 1.13 (6H, s, 3,5-CH₃); 0.9-1.9 (8H, m, 4-CH₂, 2,6-CH and PhCH₂CH₂CH₂); 2.15 (2H, d, 14.5 Hz, 2,6-CH); 2.56 (2H, t, 8 Hz, PhCH₂CH₂CH₂); 3.93 (2H, s, CH₂Cl); 6.5 (1H, br s, NH) and 7.1-7.4 ppm. (5H, m, Ph).

c) 4-{1-[(2-Chloroacetyl)amino]-3,3,5,5-tetramethylcyclohexyl}butanoic acid (22-2)

Prepared in 74% yield from amide 21-2 according to the procedure described in Example 9a. Colorless solid with mp 140-141° C.

$^1$H-NMR (CDCl₃, TMS) δ: 0.91 (6H, s, 3,5-CH₃); 1.15 (6H, s, 3,5-CH₃); 0.9-1.8 (8H, m, 4-CH₂, 2,6-CH OCCH₂CH₂CH₂); 2.17 (2H, d, 14.2 Hz, 2,6-CH); 2.33 (2H, t, 7.2 Hz, OCCH₂CH₂CH₂); 3.97 (2H, s, CH₂Cl) and 6.6 ppm. (1H, br s, NH).

d) Ethyl 4-{1-[(2-chloroacetyl)amino]-3,3,5,5-tetramethylcyclohexyl}butanoate (23-2)

Prepared in 98% yield from acid 22-2 according to the procedure described in Example 9b. A colorless oil.

$^1$H-NMR (CDCl$_3$, TMS) δ: 0.91 (6H, s, 3,5-CH$_3$); 1.14 (6H, s, 3,5-CH$_3$); 1.25 (3H, t, 7 Hz, CH$_3$CH$_2$O); 0.9-1.8 (4H, m, 4-CH$_2$, 2,6-CH, OCCH$_2$CH$_2$CH$_2$); 2.18 (2H, d, 15 Hz, 2,6-CH); 2.26 (2H, t, 8.4 Hz, OCCH$_2$CH$_2$CH$_2$); 3.95 (2H, s, CH$_2$Cl); 4.13 (2H, q, 7 Hz, CH$_3$CH$_2$O) and 6.52 ppm. (1H, br s, NH).

e) 8,8,10,10-Tetramethyl-1-azaspiro[5.5]undecan-2-one (24-2)

Prepared in 76% yield from ester 23-2 according to the procedure described in Example 9c. Colorless solid with mp 126-128° C.

$^1$H-NMR (CDCl$_3$, TMS) δ: 1.01 (6H, s, 8,10-CH$_3$); 1.09 (6H, s, 8,10-CH$_3$); 1.19 and 1.30 (both 1H, d, 14 Hz, 9-CH$_2$); 1.39 and 1.46 (both 2H, d, 14 Hz, 7,11-CH$_2$); 1.63-1.90 (4H, m, 4,5-CH$_2$); 2.33 (2H, t, 6 Hz, 3-CH$_2$) and 5.8 ppm. (1H, br s, NH).

f) 8,8,10,10-Tetramethyl-1-azaspiro[5.5]undecane hydrochloride (3-2)

Prepared in 45% yield from spirolactam 24-2 according to the procedure described in Example 9d. A colorless solid.

$^1$H-NMR (CDCl$_3$, TMS) δ: 1.01 (6H, s, 8,10-CH$_3$); 1.09 (6H, s, 8,10-CH$_3$); 1.0-2.1 (12H, m, 3,4,5,7,9,11-CH$_2$); 3.1 (2H, br s, 2-CH$_2$ and 9.1 ppm. (2H, br s, NH$_2^+$).

Overall synthetic scheme and table for 6-azatricyclo [6.3.1.0$^{1,6}$] dodecanes (belonging to the structure of formula 2 of the Summary).

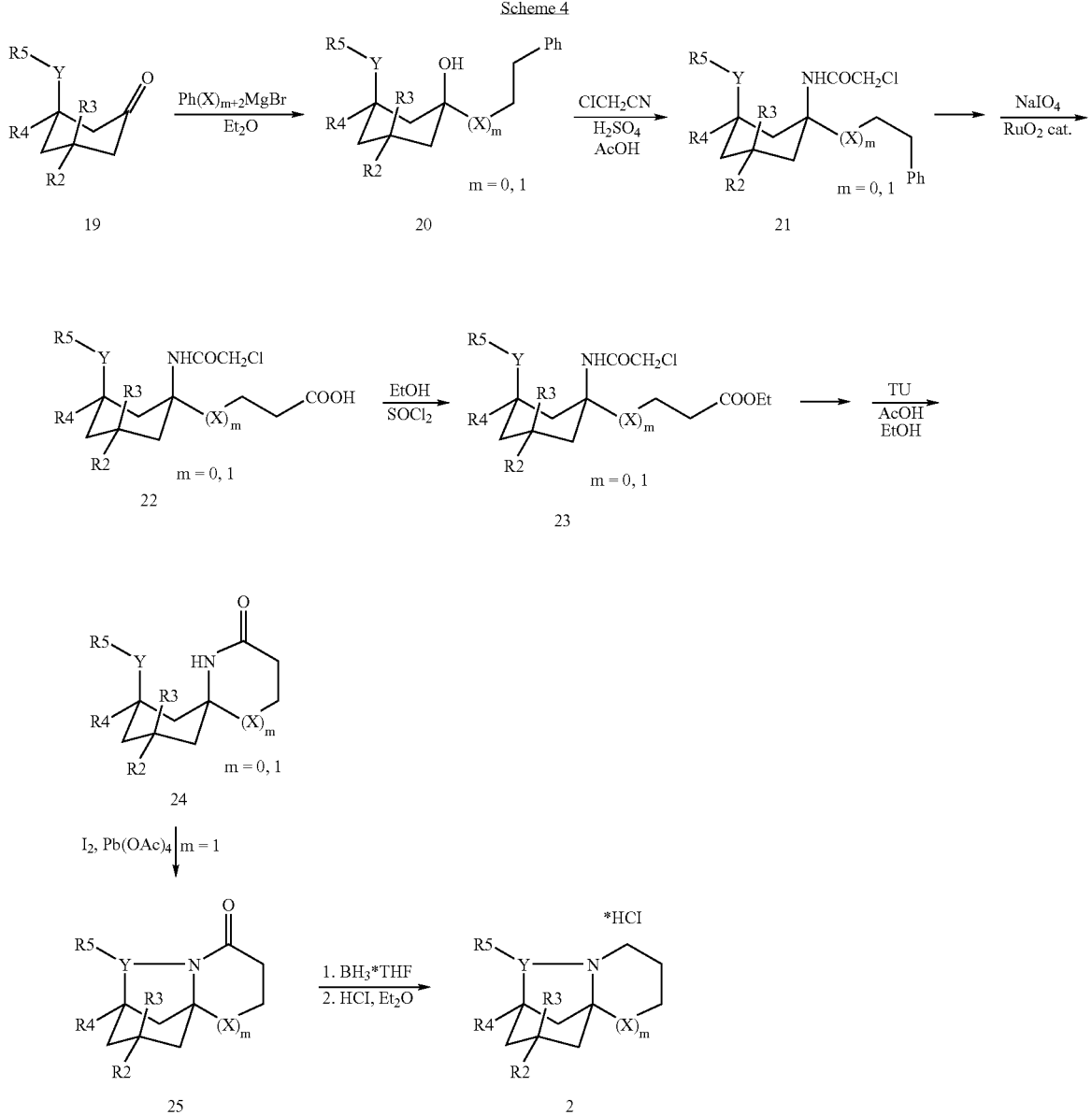

Scheme 4

TABLE 4

| MRZ number | number in synthetic description | R | $R^1$ | $R^2$ | $R^3$ | $R^4$ | $R^5$ | Y | n |
|---|---|---|---|---|---|---|---|---|---|
| 2047 | 2 | —(CH$_2$)$_4$—, (m = 1) | | Me | Me | Me | H | CH | 0 |

EXAMPLE 12

8,10,10-Trimethyl-6-azatricyclo[6.3.1.0$^{1,6}$]dodecane hydrochloride (2)

a) 8,10,10-Trimethyl-6-azatricyclo[6.3.1.0$^{1,6}$]dodecan-5-one (25)

Prepared in 20% yield from spirolactam 24-2 according to the procedure described in Example 3b. An oil.

$^1$H-NMR (CDCl$_3$, TMS) δ: 0.95 (3H, s, 10-CH$_3$); 1.00 (3H, s, 10-CH$_3$); 1.08 (3H, s, 8-CH$_3$); 1.20 (1H, d, 12 Hz) and 1.25-1.70 (5H, m, 9,11,12 CH$_2$); 1.75-1.90 (4H, m, 2,3-CH$_2$); 2.25-2.40 (2H, m, 4-CH$_2$); 3.14 and 3.43 ppm (both 1H, d, 12.0 Hz, 7-CH$_2$).

b) 8,10,10-Trimethyl-6-azatricyclo[6.3.1.0$^{1,6}$]dodecane hydrochloride (2)

Prepared in 36% yield from lactam 25 according to the procedure given in Example 9d. A colorless solid.

$^1$H-NMR (CDCl$_3$, TMS) δ: 0.85-2.45 (12H, m, 2,3,4,9, 11,12-CH$_2$); 0.99 (3H, s, 10-CH$_3$); 1.05 (3H, s, 10-CH$_3$); 1.19 (3H, s, 8-CH$_3$); 3.12 (2H, m, 5-CH$_2$); 3.20-3.75 (2H, m, 7-CH$_2$) and 9.05 ppm. (1H, br s, NH$^+$).

Pharmaceutical Compositions

The active ingredients of the invention, together with one or more conventional adjuvants, carriers, or diluents, may be placed into the form of pharmaceutical compositions and unit dosages thereof, and in such form may be employed as solids, such as coated or uncoated tablets or filled capsules, or liquids, such as solutions, suspensions, emulsions, elixirs, or capsules filled with the same, all for oral use; in the form of suppositories or capsules for rectal administration or in the form of sterile injectable solutions for parenteral (including intravenous or subcutaneous) use. Such pharmaceutical compositions and unit dosage forms thereof may comprise conventional or new ingredients in conventional or special proportions, with or without additional active compounds or principles, and such unit dosage forms may contain any suitable effective amount of the active ingredient commensurate with the intended daily dosage range to be employed. Tablets containing twenty (20) to one hundred (100) milligrams of active ingredient or, more broadly, ten (10) to two hundred fifty (250) milligrams per tablet, are accordingly suitable representative unit dosage forms.

Method of Treating

Due to their high degree of activity and their low toxicity, together presenting a most favorable therapeutic index, the active principles of the invention may be administered to a subject, e.g., a living animal (including a human) body, in need thereof, for the treatment, alleviation, or amelioration, palliation, or elimination of an indication or condition which is susceptible thereto, or representatively of an indication or condition set forth elsewhere in this application, preferably concurrently, simultaneously, or together with one or more pharmaceutically-acceptable excipients, carriers, or diluents, especially and preferably in the form of a pharmaceutical composition thereof, whether by oral, rectal, or parental (including intravenous and subcutaneous) or in some cases even topical route, in an effective amount. Suitable dosage ranges are 1-1000 milligrams daily, preferably 10-500 milligrams daily, and especially 50-500 milligrams daily, depending as usual upon the exact mode of administration, form in which administered, the indication toward which the administration is directed, the subject involved and the body weight of the subject involved, and the preference and experience of the physician or veterinarian in charge.

EXAMPLES OF REPRESENTATIVE PHARMACEUTICAL COMPOSITIONS

With the aid of commonly used solvents, auxiliary agents and carriers, the reaction products can be processed into tablets, coated tablets, capsules, drip solutions, suppositories, injection and infusion preparations, and the like and can be therapeutically applied by the oral, rectal, parenteral, and additional routes. Representative pharmaceutical compositions follow.

(a) Tablets suitable for oral administration which contain the active ingredient may be prepared by conventional tabletting techniques.

(b) For suppositories, any usual suppository base may be employed for incorporation thereinto by usual procedure of the active ingredient, such as a polyethyleneglycol which is a solid at normal room temperature but which melts at or about body temperature.

(c) For parental (including intravenous and subcutaneous) sterile solutions, the active ingredient together with conventional ingredients in usual amounts are employed, such as for example sodium chloride and double-distilled water q.s., according to conventional procedure, such as filtration, aseptic filling into ampoules or IV-drip bottles, and autoclaving for sterility.

Other suitable pharmaceutical compositions will be immediately apparent to one skilled in the art.

The following examples are again given by way of illustration only and are not to be construed as limiting.

Example 1

Tablet Formulation

A suitable formulation for a tablet containing 10 milligrams of active ingredient is as follows:

| | Mg. |
|---|---|
| Active Ingredient | 10 |
| Lactose | 63 |
| Microcrystalline Cellulose | 21 |
| Talcum | 4 |
| Magnesium stearate | 1 |
| Colloidal silicon dioxide | 1 |

Example 2

Tablet Formulation

Another suitable formulation for a tablet containing 100 mg is as follows:

|  | Mg. |
| --- | --- |
| Active Ingredient | 100 |
| Potato starch | 20 |
| Polyvinylpyrrolidone | 10 |
| Film coated and colored. | |
| The film coating material consists of: | |
| Lactose | 100 |
| Microcryst. Cellulose | 80 |
| Gelatin | 10 |
| Polyvinylpyrrolidone, crosslinked | 10 |
| Talcum | 10 |
| Magnesium stearate | 2 |
| Colloidal silicon dioxide | 3 |
| Color pigments | 5 |

Example 3

Capsule Formulation

A suitable formulation for a capsule containing 50 milligrams of active ingredient is as follows:

|  | Mg. |
| --- | --- |
| Active Ingredient | 50 |
| Corn starch | 20 |
| Dibasic calcium phosphate | 50 |
| Talcum | 2 |
| Colloidal silicon dioxide | 2 |
| filled in a gelatin capsule. | |

Example 4

Solution for Injection

A suitable formulation for an injectable solution containing one percent of active ingredient is as follows:

| | |
| --- | --- |
| Active Ingredient mg | 12 |
| Sodium chloride mg | 8 |
| Sterile water to make ml | 1 |

Example 5

Liquid Oral Formulation

A suitable formulation for 1 liter of a liquid mixture containing 2 milligrams of active ingredient in one milliliter of the mixture is as follows:

|  | G. |
| --- | --- |
| Active Ingredient | 2 |
| Saccharose | 250 |
| Glucose | 300 |
| Sorbitol | 150 |
| Orange flavor | 10 |
| Sunset yellow. | |
| Purified water to make a total of 1000 ml. | |

Example 6

Liquid Oral Formulation

Another suitable formulation for 1 liter of a liquid mixture containing 20 milligrams of active ingredient in one milliliter of the mixture is as follows:

|  | G. |
| --- | --- |
| Active Ingredient | 20.00 |
| Tragacanth | 7.00 |
| Glycerol | 50.00 |
| Saccharose | 400.00 |
| Methylparaben | 0.50 |
| Propylparaben | 0.05 |
| Black currant-flavor | 10.00 |
| Soluble Red color | 0.02 |
| Purified water to make a total of 1000 ml. | |

Example 7

Liquid Oral Formulation

Another suitable formulation for 1 liter of a liquid mixture containing 2 milligrams of active ingredient in one milliliter of the mixture is as follows:

|  | G. |
| --- | --- |
| Active Ingredient | 2 |
| Saccharose | 400 |
| Bitter orange peel tincture | 20 |
| Sweet orange peel tincture | 15 |
| Purified water to make a total of 1000 ml. | |

Example 8

Aerosol Formulation 180 g aerosol solution contain:

|  | G. |
| --- | --- |
| Active Ingredient | 10 |
| Oleic acid | 5 |
| Ethanol | 81 |
| Purified Water | 9 |
| Tetrafluoroethane | 75 |

15 ml of the solution are filled into aluminum aerosol cans, capped with a dosing valve, purged with 3.0 bar.

Example 9

TDS Formulation 100 g solution contain:

|  | G. |
| --- | --- |
| Active Ingredient | 10.0 |
| Ethanol | 57.5 |
| Propyleneglycol | 7.5 |
| Dimethylsulfoxide | 5.0 |
| Hydroxyethylcellulose | 0.4 |
| Purified water | 19.6 |

1.8 ml of the solution are placed on a fleece covered by an adhesive backing foil. The system is closed by a protective liner which will be removed before use.

Example 10

Nanoparticle Formulation 10 g of polybutylcyanoacrylate nanoparticles contain:

|  | G. |
| --- | --- |
| Active Ingredient | 1.00 |
| Poloxamer | 0.10 |
| Butylcyanoacrylate | 8.75 |
| Mannitol | 0.10 |
| Sodiumchloride | 0.05 |

Polybutylcyanoacrylate nanoparticles are prepared by emulsion polymerization in a water/0.1 N HCl/ethanol mixture as polymerizsation medium. The nanoparticles in the suspension are finally lyophilized under vacuum.

PHARMACOLOGY-SUMMARY

The active principles of the present invention, and pharmaceutical compositions thereof and method of treating therewith, are characterized by unique advantageous and unpredictable properties, rendering the "subject matter as a whole", as claimed herein, unobvious. The compounds and pharmaceutical compositions thereof have exhibited, in standard accepted reliable test procedures, the following valuable properties and characteristics:

They are systemically-active, uncompetitive NMDA receptor antagonists with rapid blocking/unblocking kinetics and strong voltage dependency and are, accordingly, of utility in the treatment, elimination, palliation, alleviation, and amelioration of responsive conditions, by application or administration to the living animal host for the treatment of a wide range of CNS disorders which involve disturbances of glutamatergic transmission.

These compounds are also systemically-active, non-competitive $5HT_3$ and neuronal nicotinic receptor antagonists and are, accordingly, of utility in the treatment, elimination, palliation, alleviation, and amelioration of responsive conditions, by application or administration to the living animal host for the treatment of a wide range of CNS disorders which involve disturbances of serotonin or nicotinic transmission.

Methods

Receptor Binding Studies

Male Sprague-Dawley rats (200-250 g) were decapitated and their brains were removed rapidly. The cortex was dissected and homogenized in 20 volumes of ice-cold 0.32 M sucrose using a glass-Teflon homogenizer. The homogenate was centrifuged at 1000× g for 10 min. The pellet was discarded and the supernatant centrifuged at 20,000× g for 20 min. The resulting pellet was re-suspended in 20 volumes of distilled water and centrifuged for 20 min at 8000× g. Then the supernatant and the buffy coat were centrifuged at 48,000× g for 20 min in the presence of 50 mM Tris-HCl, pH 8.0. The pellet was then re-suspended and centrifuged two to three more times at 48,000× g for 20 min in the presence of 50 mM Tris-HCl, pH 8.0. All centrifugation steps were carried out at 4° C. After resuspension in 5 volumes of 50 mM Tris-HCl, pH 8.0 the membrane suspension was frozen rapidly at −80° C.

On the day of assay the membranes were thawed and washed four times by resuspension in 50 mM Tris-HCl, pH 8.0 and centrifugation at 48,000× g for 20 min. and finally re-suspended in 50 mM Tris-HCl, pH 7.4. The amount of protein in the final membrane preparation (250-500 µg/ml) was determined according to the method of Lowry et al. (1951). Incubations were started by adding [$^3$H]-(+)-MK-801 (23.9 Ci/mmol, 5 nM, Dupont NEN) to vials with glycine (10 µM), glutamate (10 µM), and 125-250 µg protein (total volume 0.5 ml) and various concentrations of the agents tested (10 concentrations in duplicates). The incubations were continued at room temperature for 120 min (equilibrium was achieved under the conditions used). Non-specific binding was defined by the addition of unlabeled (+)-MK-801 (10 µM). Incubations were terminated using a Millipore filter system. The samples were rinsed twice with 4 ml of ice cold assay buffer over glass fibre filters (Schleicher & Schuell) under a constant vacuum. Following separation and rinse the filters were placed into scintillation liquid (5 ml; Ultima Gold) and radioactivity retained on the filters was determined with a conventional liquid scintillation counter (Hewlett Packard, Liquid Scintillation Analyser). The Kd of [$^3$H]-(+)-MK-801 of 4.6 nM was determined by Scatchard analysis and used according to the Cheng Prussoff relationship to calculate the affinity of displacers as Kd values. Most antagonists were tested in 3 to 7 separate experiments.

NMDA and Neuronal Nicotinic Receptor Subtype Expression in *Xenopus Oocytes*

Mature female *Xenopus laevis* were anaesthetized in 0.2% Tricaine on ice for 15 min prior to surgery. Oocytes were removed and incubated in 2 mg/ml collagenase (type II) in $Ca^{2+}$-free oocyte Ringer solution (82.5 mM NaCl, 2 mM KCl, 2 mM $MgCl_2$, 5 mM HEPES, pH 7.5) for 30 min. at room temperature and washed thoroughly with OR-2 (100 mM NaCl, 2 mM KCl, 1 mM $MgCl_2$, 2 mM $CaCl_2$, 5 mM HEPES, pH 7.5). The remaining follicle cell layer was removed manually with fine forceps and the oocytes were kept in OR-2. The RNA was dissolved in DEPC-treated, sterile distilled water. RNA for the NMDA NR1a subunit was mixed 1:1 with RNA for the NR2A subunit. Likewise neuronal nicotinic α4 RNA was mixed 1:1 with RNA for the β2 subunit. Fifty to 100 nanoliters of each RNA mixture were injected in the oocyte's cytoplasm using a Nanoliter Injector (World Precision Instruments). The oocytes were incubated at 19° C. in OR-2 for the following 3 to 6 days.

The electrophysiological responses were obtained using the standard two-electrode voltage-clamp method (GeneClamp 500 amplifier), 2-6 days after injection. The electrodes had a resistance between 0.2 and 0.4 MΩ and were filled with 3M KCl. Recordings were made in a custom made chamber with 2 to 3 second exchange times. The bath solution was prepared $Ca^{2+}$-free, to avoid $Ca^{2+}$-induced $Cl^-$ currents (100 mM NaCl, 2 mM KCl, 5 mM HEPES, 2 mM $BaCl_2$, pH 7.35). NMDA receptors were activated by the manual co-application of 1 mM Glutamate and 10 μM Glycine for 30-40 secs every 2 to 3 mins to oocytes clamped at −70 mV. Neuronal nicotinic receptors were activated by application of 100 μM acetylcholine for 20-30 secs every 2 to 3 mins to oocytes clamped at −70 mV. After obtaining stable control responses, full concentration-response curves with antagonists were obtained by preincubating 6-7 different concentrations at log 3 intervals.

Only results from stable cells were accepted for inclusion in the final analysis i.e. showing at least 50% recovery of responses to NMDA following removal of the antagonist tested. Despite this, recovery from drug actions wasn't always 100% because of minor rundown or runup in some cells. When present, this was always compensated by basing the % antagonism at each concentration on both control and recovery and assuming a linear time course for this rundown. All antagonists were assessed at steady-state blockade with 6 to 7 concentrations on at least 4 cells. Equilibrium blockade was achieved within 1 to 3 agonist applications, depending on antagonist concentration.

Kinetic experiments were performed by applying various concentrations of unsaturated amino-alkyl-cyclohexanes (normally 5 in a log 3 dosing regime) for 10-20 seconds in the continuous presence of glutamate (100 μM and glycine 10 μM) for 90-180 seconds in Xenopus oocytes expressing NR1a/2A receptors. The perfusion system used for these experiments was a modified oocyte carousel system which allows rapid wash in and wash out of agonist and antagonist with change times less than one second. Exponential fits were made using the program TIDA for windows and most responses were well fitted by a single exponential. This same system was used to access the voltage-dependency of blockade, but the bath solution contained flufenamic acid (100 μM) to block endogenous voltage-activated and $Ca^{2+}$ activated $Cl^-$ currents. Also, $Ba^{2+}$ (2 mM) was replaced by low concentrations of $Ca^{2+}$ (0.2 mM). Following equilibrium blockade by higher concentrations of antagonist (normally around 10 times the $IC_{50}$), five ramps were driven from −70 mV to +30 mV over two seconds. Similar ramps were driven in bath solutions and for glutamate without antagonist, both before antagonist application and following recovery of responses. The leak currents in the absence of glutamate were substrated from the glutamate and glutamate plus antagonist curves. Voltage-dependency was then determined by comparing the glutamate and glutamate plus antagonist curves.

Patch Clamp for NMDA and Nicotine

Hippocampi were obtained from rat embryos (E20 to E21) and were then transferred to calcium and magnesium free Hank's buffered salt solution (Gibco) on ice. Cells were mechanically dissociated in 0.05% DNAase/0.3% ovomucoid (Sigma) following an 8 minute pre-incubation with 0.66% trypsin/0.1% DNAase (Sigma). The dissociated cells were then centrifuged at 18× g for 10 minutes, re-suspended in minimum essential medium (Gibco) and plated at a density of 150,000 cells $cm^{-2}$ onto poly-L-lysine (Sigma)-precoated plastic petri dishes (Falcon). The cells were nourished with $NaHCO_3$/HEPES-buffered minimum essential medium supplemented with 5% fetal calf serum and 5% horse serum (Gibco) and incubated at 37°C. with 5% $CO_2$ at 95% humidity. The medium was exchanged completely following inhibition of further glial mitosis with cytosine-Я-D-arabinofuranoside (20 μM Sigma) after about 7 days in vitro. Thereafter the medium was exchanged partially twice weekly.

Patch clamp recordings were made from these neurones with polished glass electrodes (4-6 mΩ) in the whole cell mode at room temperature (20-22°C.) with the aid of an EPC-7 amplifier (List). Test substances were applied by switching channels of a custom-made fast superfusion system with a common outflow (10-20 ms exchange times). The contents of the intracellular solution were as follows (mM): CsCl (120), TEACl (20), EGTA (10), $MgCl_2$(1), $CaCl_2$(0.2), glucose (10), ATP(2), cAMP (0.25); pH was adjusted to 7.3 with CsOH or HCl. The extracellular solutions had the following basic composition (mM): NaCl (140), KCl (3), $CaCl_2$ (0.2), glucose (10), HEPES (10), sucrose (4.5), tetrodotoxin (TTX $3*10^{-4}$). Glycine (1 μM) was present in all solutions: a concentration sufficient to cause around 80-85% activation of $glycine_B$ receptors. Only results from stable cells were accepted for inclusion in the final analysis, i.e., following recovery of responses to NMDA by at least 75% of their depression by the antagonists tested.

Patch Clamp for 5-HT3

N1E-115 cells were purchased from the European collection of cell cultures (ECACC, Salisbury, UK) and stored at −80°C. until further use. The cells were plated at a density of 100,000 cells $cm^{-2}$ onto plastic Petri dishes (Falcon) and were nourished with $NaHCO_3$/HEPES-buffered minimum essential medium supplemented (MEM) with 15% fetal calf serum (Gibco) and incubated at 37°C. with 5% $CO_2$ at 95% humidity. The medium was exchanged completely daily. Once every three days, cells were reseeded onto fresh Petri dishes following treatment with trypsin-EDTA (1% in PBS), resuspension in MEM and centrifugation at 1000 rpm for four minutes.

Patch clamp recordings at −70 mV were made from lifted cells, 2-3 days following seeding with polished glass electrodes (2-6MΩ) in the whole cell mode at room temperature (20-22°C.) with an EPC-7 amplifier (List). The contents of the intracellular solution were as follows (mM): CsCl (130), HEPES (10), EGTA (10), $MgCl_2$ (2), $CaCl_2$ (2), K-ATP (2), Tris-GTP (0.2), D-glucose (10); pH was adjusted to 7.3 with CsOH or HCl. The extracellular solutions had the following basic composition (mM): NaCl (124), KCl (2.8), HEPES (10), pH 7.3 adjusted with NaOH or HCl.

After the whole-cell configuration was established, the cells were lifted from the glass substrate and serotonin (10 μM), mezzanine and unsaturated amino-alkyl-cyclohexane derivatives were applied at various concentrations using a fast superfusion device. A piezo translator-driven double-barrelled application pipette was used to expose the lifted cell either to serotonin-free or serotonin-containing solution. A two second serotonin pulse was delivered every 60 seconds. The putative antagonists were dissolved in aquabidest and diluted with bath solution to the desired concentration. Only results from stable cells were accepted for inclusion in the final analysis, i.e., showing at least 50% recovery of responses to serotonin following removal of compounds. Despite this, recovery from drug actions wasn't always 100% because of rundown in some cells (<=10% over 10 minutes). When present, this was always compensated by basing the percent antagonism at each concentration on both control and recovery and assuming a linear time course for this rundown. All antagonists were assessed at steady-state blockade with 3 to 6 concentrations on at least five cells. Equilibrium blockade was achieved within 2 to 5 agonist applications, depending on antagonist concentration.

In Vivo

Anticonvulsive Activity

NMR female mice (18-28 g) housed 5 per cage were used for the maximal electroshock (MES) and motor impairment tests. All animals were kept with water and food ad libitum under a 12 hour light-dark cycle (light on at 6 a.m.) and at a controlled temperature (20±0.5°C.). All experiments were performed between 10 a.m. and 5 p.m. Tested agents were injected 30 min. i.p. before the induction of convulsions if not stated otherwise (see below). All compounds were dissolved in 0.9% saline.

The MES test was performed together with tests for myorelaxant action (traction reflex) and motor coordination (rotarod). For the traction reflex test mice were placed with their forepaws on a horizontal rod and were required to place all 4 paws on the wire within 10 seconds. To test ataxia (motor coordination) mice were placed on an accelerating rotarod and were required to remain on the rod for 1 minute. Only mice not achieving the criteria in all three repetitions of each test were considered to exhibit myorelaxation or ataxia respectively. These tests were followed by MES (100 Hz, 0.5 second shock duration, 50 mA shock intensity, 0.9 ms impulse duration, Ugo Basile) applied through corneal electrodes. The presence of tonic convulsions was scored (tonic extension of hind paws with minimum angle to the body of 90°). The aim was to obtain $ED_{50}$ for all parameters scored (anticonvulsive activity and motor side effects) with use of the Litchfield Wilcoxon test for quantal dose responses. Division of the $ED_{50}$ for side effects (ataxia or myorelaxation) by the $ED_{50}$ for antagonism of electroshock convulsions was used as a therapeutic index (TI).

Statistical Analysis $IC_{50}$s in patch clamp and binding studies were calculated according to the four parameter logistic equation using the Grafit computer program (Erithacus Software, England). Ki value for binding studies were then determined according to Cheng and Prusoff. Binding values presented are means±SEM of 3-5 determinations (each performed in duplicate).

4-7 doses of antagonists were tested in each of the in vivo tests (5-8 animals per dose) to allow calculation of graded $ED_{50}$s according to probit analysis (Litchfield and Wilcoxon) with correction for 0% to 100% effects. $ED_{50}$s are presented with 95% confidence limits (Cl). Pearson product moment correlation analysis (Sigma Stat, Jandel Scientific) was used to compare in vitro potencies and in vivo anticonvulsant activity.

RESULTS

MRZ Numbers

MRZ numbers are used to represent chemical names. The MRZ numbers and their respective chemical names are shown in "MRZ LIST", and are cross-referenced in the Examples

MRZ LIST

| MRZ | Chemical Name |
| --- | --- |
| 2/1013 | 8,8,10,10-Tetramethyl-1-azaspiro[5.5]undecane hydrochloride |
| 2/1004 | 7,7,9,9-Tetramethyl-1-azaspiro[4.5]decane hydrochloride |
| 2/1003 | 1,3,3,5,6-Pentamethyl-6-azabicyclo [3.2.1]octane hydrochloride |
| 2/1010 | 1,3,3,5-Tetramethyl-6-azabicyclo [3.2.1]octane hydrochloride |
| 2007 | exo-3-Ethyl-1,5-dimethyl-6-azabicyclo[3.2.1]octane hydrochloride |
| 2011 | 1,exo-3,5-Trimethyl-6-azabicyclo[3.2.1]octane hydrochloride |
| 2022 | 5-Ethyl-1,3,3-trimethyl-6-azabicyclo[3.2.1]octane hydrochloride |
| 2023 | 5-Ethyl-1,exo-3-dimethyl-6-azabicyclo[3.2.1]octane hydrochloride |
| 2028 | 1,exo-3,5-Trimethyl-exo,endo-7-phenyl-6-azabicyclo[3.2.1]octane hydrochloride |
| 2029 | 1,exo-3,5,exo,endo-7-Tetramethyl-6-azabicyclo[3.2.1]octane hydrochloride |
| 2046 | 1,5,exo-7-Trimethyl-2-azabicyclo[3.3.1]nonane hydrochloride |
| 2047 | 8,10,10-Trimethyl-6-azatricyclo[6.3.1.0$^{1,6}$]dodecane hydrochloride |

Binding MK-801

All compounds displaced [$^3$H]-(+)-MK-801 with Ki values between 1 and 83 μM (see Table 1).

TABLE 1

| MRZ | Group | [3H]MK-801 Ki | SEM | n | NMDA IC50 (μM) | SEM | N |
| --- | --- | --- | --- | --- | --- | --- | --- |
| 2/1004 | Bicyclic | 10.46 | 1.05 | 3 | | | |
| 2/1013 | Bicyclic | 3.64 | 0.22 | 3 | 4.72 | 0.05 | 6 |
| 2/1003 | Bridged 579 | 7.40 | 0.52 | 3 | | | |
| 2/1010 | Bridged 579 | 2.59 | 0.17 | 3 | 0.76 | 0.12 | 6 |
| 2007 | Bridged 579 | 5.46 | 0.22 | 3 | 6.77 | 0.36 | 6 |
| 2011 | Bridged 579 | 15.82 | 0.94 | 3 | | | |
| 2022 | Bridged 579 | 14.42 | 1.94 | 3 | 13.87 | 2.30 | 6 |
| 2023 | Bridged 579 | 23.32 | 2.52 | 3 | 16.11 | 3.29 | 6 |
| 2028 | Bridged 579 | 3.21 | 0.08 | 3 | 10.33 | 0.42 | 6 |
| 2029 | Bridged 579 | 13.22 | 1.28 | 3 | 36.11 | 1.61 | 6 |
| 2046 | | | | | | | |
| 2047 | | | | | | | |

The results for representative compounds are reported in FIG. 1.

NMDA Receptor Subtype Expression In *Xenopus Oocytes*.

Figure 2:
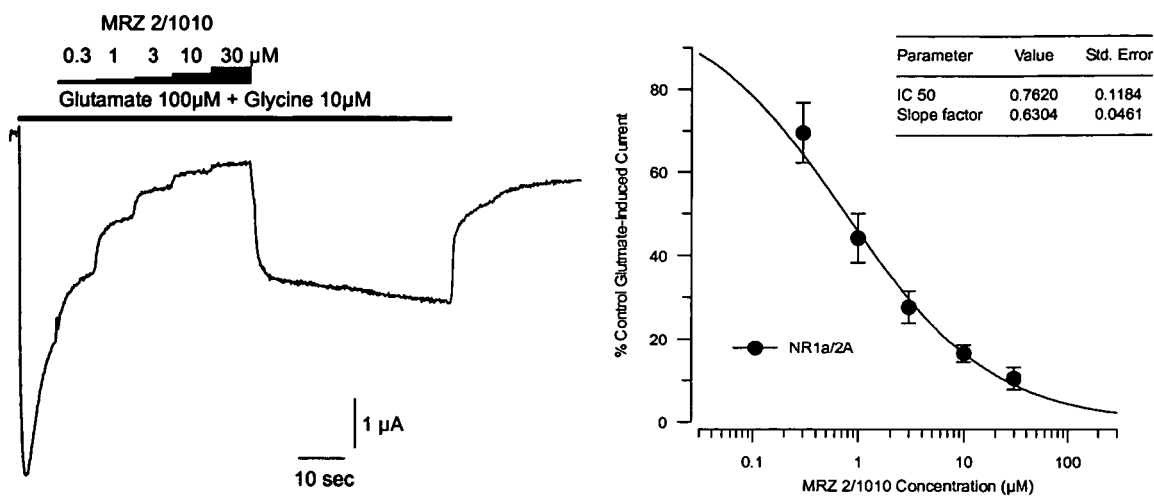
FIG. 2 shows NMDA subtype expression in *xenopus* oocytes.

NMDA receptor blockade by MRZ 2/1010 was determined by applying various concentrations (0.3 to 30 µM in a log 3 dosing regime) for 10 seconds in the continuous presence of glutamate (100 µM) and glycine 10 µM) at –70 mV for 100 seconds in *Xenopus oocytes* expressing NR1a/2A receptors (FIG. 2, left). The potency of MRZ 2/1010 ($IC_{50}$=0.76 µM, Hill 0.63) was determined by plotting percent blockade against antagonist concentration and then fitting the curve according to the logistic equation (FIG. 2, right).

Invivo

Anti-Convulsive Activity

MES and Myorelaxant action results are presented in Table 2.

systemically-active, uncompetitive NMDA receptor antagonists with rapid blocking/unblocking kinetics and strong voltage-dependency. In view of their moderate potency and associated rapid kinetics, they will be useful therapeutics in a wide range of CNS disorders which involve disturbances of glutamatergic transmission.

These compounds accordingly find application in the treatment of the following disorders of a living animal body, especially a human. 1. Excitotoxicity such as ischemia during stroke, trauma, hypoxia, hypoglycemia, glaucoma, and hepatic encephalopathy. 2. Chronic neurodegenerative diseases such as Alzheimer's disease, vascular dementia, Parkinson's disease, Huntington's disease, multiple sclerosis, amyotrophic lateral sclerosis, AIDS-neurodegeneration, olivopontocerebellar atrophy, Tourette's syndrome, motor neurone disease, mitochondrial dysfunction, Korsakoff syndrome, Creutzfeldt-Jakob disease. 3. Other disorders related to long term plastic changes in the central nervous system

TABLE 2

| MRZ | MES ED50 | MES CL | Myorelaxation ED50 | Myorelaxation CI | Ataxia ED50 | Ataxia CI | TI Myorelaxation | TI Ataxia |
|---|---|---|---|---|---|---|---|---|
| 2/1003 | 16.25 | 9–29.4 | 16.77 | 11–25.5 | 20.60 | 14.6–29.1 | 1.03 | 1.27 |
| 2/1004 | 24.07 | 7.3–79 | 27.52 | 24.5–30.9 | 24.03 | 16.5–34.9 | 1.14 | 1.00 |
| 2/1010 | 5.91 | 3.4–10.3 | 10.62 | 8.1–13.9 | 24.86 | 15.5–39.8 | 1.80 | 4.21 |
| 2/1013 | 9.39 | 2.6–33.8 | 34.49 | 21.9–54.2 | 37.24 | 30.5–45.5 | 3.67 | 3.97 |
| 2007 | >50 | | >50 | | 50.00 | | | |
| 2011 | | | | | | | | |
| 2022 | | | | | | | | |
| 2023 | >30 | | >30 | | >30 | | | |
| 2028 | | | | | | | | |
| 2029 | >50 | | >50 | | >50 | | | |
| 2046 | | | | | | | | |
| 2047 | | | | | | | | |

In conclusion, from the foregoing, it is apparent that the present invention provides novel, valuable, and unpredictable applications and uses of the compounds of the present invention, which compounds comprise the active principle according to the present invention, as well as novel pharmaceutical compositions thereof and methods of preparation thereof and of treating therewith, all possessed of the foregoing more specifically-enumerated characteristics and advantages.

The high order of activity of the active agent of the present invention and compositions thereof, as evidenced by the tests reported, is indicative of utility based on its valuable activity in human beings as well as in lower animals. Clinical evaluation in human beings has not been completed, however. It will be clearly understood that the distribution and marketing of any compound or composition falling within the scope of the present invention for use in human beings will of course have to be predicated upon prior approval by governmental agencies, such as the U.S. Federal Food and Drug Administration, which are responsible for and authorized to pass judgment on such questions.

CONCLUSIONS

The instant azabicyclic, azatricyclic and azaspirocyclic derivatives of aminocyclohexanes represent a novel class of selected from chronic pain, drug tolerance, dependence and addiction (e.g., opioids, cocaine, benzodiazepines, nicotine, and alcohol). 4. Epilepsy, tardive dyskinesia, schizophrenia, anxiety, depression, acute pain, spasticity, and tinnitus.

Furthermore, it was found that these compounds are neuronal nicotinic receptor and $5HT_3$ receptor antagonists as well. The compounds of the invention thus find application in the treatment of disorders in a living animal body, especially a human, in both nicotinic and $5HT_3$ receptor mediated indications for both symptomatic and neuroprotective purposes (e.g. emesis, nicotine abuse, schizophrenia, cerebellar tremor, IBS, migraine, depressive disorders, cognitive disorders, Parkinson's disease treatment-related psychosis and appetite disorders).

In addition, as already stated, due to at least in part to their amine substituent, the compounds of the present invention are also effective in indications not related to the aforementioned mechanism of action, exhibiting immunomodulatory activity, anti malaria and antitrypanozomal potency, anti-Borne virus, anti-HSV and anti-Hepatitis C virus activity.

The method-of-treating a living animal body with a compound of the invention, for the inhibition of progression or alleviation of the selected ailment therein, is as previously stated by any normally-accepted pharmaceutical route, employing the selected dosage which is effective in the alleviation of the particular ailment desired to be alleviated.

Use of the compounds of the present invention in the manufacture of a medicament for the treatment of a living animal for inhibition of progression or alleviation of selected ailments or conditions, particularly ailments or conditions susceptible to treatment with an NMDA receptor antagonist, neuronal nicotinic receptor antagonist, $5HT_3$ antagonist, or a compound exhibiting immunomodulatory activity, anti malaria and antitrypanosomal potency, anti-Borne virus, and anti-HSV and anti-Hepatitis C virus activity, is carried out in the usual manner comprising the step of admixing an effective amount of a compound of the invention with a pharmaceutically-acceptable diluent, excipient, or carrier, and the method-of-treating, pharmaceutical compositions, and use of a compound of the present invention in the manufacture of a medicament.

Representative pharmaceutical compositions prepared by admixing the active ingredient with a suitable pharmaceutically-acceptable excipient, diluent, or carrier, include tablets, capsules, solutions for injection, liquid oral formulations, aerosol formulations, TDS formulations, and nanoparticle formulations, thus to produce medicaments for oral, injectable, or dermal use, also in accord with the foregoing.

REFERENCES

1. R. L. Frank, H. K. Hall (1950) J. Am. Chem. Soc. 72:1645-1648.
2. G. A. Hiegel, P. Burk. (1973) J. Org. Chem. 38:3637-3639.
3. N. F. Firrell, P. W. Hickmott. (1970) J. Chem. Soc. C:716-719.
4. G. H. Posner, L. L. Frye. (1984) Isr. J. Chem. 24:88-92.
5. G. L. Lemiere, T. A. van Osselaer, F. C. Anderweireldt. (1978) Bull. Soc. Chim. Belg. 87:771-782.
6. H. O. House, J. M. Wilkins. (1976) J. Org. Chem. 41:(25) 4031-4033.
7. A. R. Greenaway, W. B. Whalley. (1976) J. Chem. Soc. P.T. 1.:1385-1389.
8. S. Matsuzawa, Y. Horiguchi, E. Nakamura, I. Kuwajima. (1989) Tetrahedron 45:(2) 349-362.
9. H. O. House, W. F. Fischer. (1968) J. Org. Chem. 33:(3) 949-956.
10. Chiurdoglu, G., Maquestiau, A. (1954) Bull. Soc. Chim. Belg. 63: 357-378.
11. Zaidlewicz, M., Uzarewicz A., Zacharewicz, W. (1964) Roczniki Chem. 38: 591-597.
12. Crossley, A. W., Gilling, C. (1910) J. Chem. Soc. 2218.
13. Zaidlewicz, M., Uzarewicz, A. (1971) Roczniki Chem. 45: 1187-1194.
14. Lutz, E. T., van der Maas, J. H. (1981) Spectrochim. Acta, A. 38A: 283.
15. Lutz, E. T., van der Maas, J. H. (1981) Spectrochim. Acta, A. 37A: 129-134.
16. Ramalingam K., Balasubramanian, M., Baliah, V. (1972) Indian J. Chem. 10: 366-369.
17. Hamlin, K. E., Freifelder, M. (1953) J. Am. Chem. Soc. 75: 369-373.
18. Hassner, A., Fibinger, R., Andisik, D. (1984) J. Org. Chem. 49: 4237-4244.
19. W. Danysz, C. G. Parsons, I. Bresink, G. Quack (1995) Drug News Perspect. 8:261-277.
20. J. D. Leander, R. R. Lawson, P. L., Ornstein, D. M. Zimmerman (1988) Brain Res. 448:115-120.
21. C. G. Parsons, G. Quack, I. Bresink, L. Baran, E. Przegalinski, W. Kostowski, P. Krzascik, S. Hartmann, W. Danysz (1995). Neuropharmacology 34:1239-1258.
22. M. A. Rogawski (1993) Trends Pharmacol. Sci. 14:325-331.
23. Booher J. and Sensenbrenner M. (1972). Neurobiology 2:97-105.
24. Dichter, M. (1987) Brain Research 149:279.

We claim:

1. Compounds of formula (1)

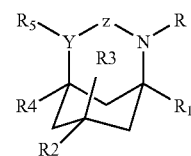

wherein

R and $R^1$ together represent a $C_3$-$C_5$ alkylene or alkenylene group, $R^2$-$R^5$ are each independently selected from hydrogen atoms, $C_1$-$C_6$ alkyl groups, $C_2$-$C_6$ alkenyl groups, $C_2$-$C_6$ alkynyl groups, $C_6$-$C_{12}$ aryl- $C_1$-$C_4$ alkyl groups, and optionally substituted $C_6$-$C_{12}$ aryl groups, with the proviso that at least one of $R^2$ and $R^3$ and at least one of $R^4$ and $R^5$ are other than hydrogen;

Y is CH; and

Z represents hydrogen atoms attached to Y and N respectively;

and pharmaceutically-acceptable acid and base addition salts thereof.

2. A method-of-treating epilepsy in a living animal comprising the step of administering to the living animal a therapeutically effective amount of a compound selected from those of formula 1,

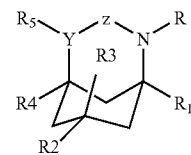

wherein

R and $R^1$ together represent a $C_3$-$C_5$ alkylene or alkenylene group, $R^2$-$R^5$ are each independently selected from hydrogen atoms, $C_1$-$C_6$ alkyl groups, $C_2$-$C_6$ alkenyl groups, $C_2$-$C_6$ alkynyl groups, $C_6$-$C_{12}$ aryl- $C_1$-$C_4$ alkyl groups, and optionally substituted $C_6$-$C_{12}$ aryl groups;

Y is CH; and

Z represents hydrogen atoms attached to Y and N respectively;

and pharmaceutically-acceptable acid and base addition salts thereof.

3. A pharmaceutical composition consisting of a compound selected from those of formula 1,

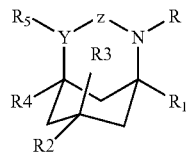

wherein

R and $R^1$ together represent a $C_3$-$C_5$ alkylene or alkenylene group, $R^2$-$R^5$ are each independently selected from hydrogen atoms, $C_1$-$C_6$ alkyl groups, $C_2$-$C_6$ alkenyl groups, $C_2$-$C_6$ alkynyl groups, $C_6$-$C_{12}$ aryl- $C_1$-$C_4$ alkyl groups, and optionally substituted $C_6$-$C_{12}$ aryl groups;

Y is CH; and

Z represents hydrogen atoms attached to Y and N respectively;

and pharmaceutically-acceptable acid and base addition salts thereof in combination with one or more pharmaceutically-acceptable diluents, excipients, or carriers.

* * * * *